US008808365B2

(12) United States Patent
Ng et al.

(10) Patent No.: US 8,808,365 B2
(45) Date of Patent: Aug. 19, 2014

(54) CHEMICALLY AND BIOLOGICALLY MODIFIED MEDICAL DEVICES

(76) Inventors: Martin Kean Chong Ng, New South Wales (AU); Anna Waterhouse, Coogee (AU); Anthony Steven Weiss, Randwick (AU); Steven Garry Wise, Sydney (AU)

( * ) Notice: Subject to any disclaimer, the term of this patent is extended or adjusted under 35 U.S.C. 154(b) by 660 days.

(21) Appl. No.: 12/652,926

(22) Filed: Jan. 6, 2010

(65) Prior Publication Data

US 2010/0174351 A1      Jul. 8, 2010

Related U.S. Application Data

(60) Provisional application No. 61/143,085, filed on Jan. 7, 2009.

(51) Int. Cl.
*A61F 2/06*        (2013.01)
*A61K 38/00*       (2006.01)

(52) U.S. Cl.
USPC ............................ 623/1.48; 623/1.44; 514/1.1

(58) Field of Classification Search
None
See application file for complete search history.

(56) References Cited

U.S. PATENT DOCUMENTS

| | | | |
|---|---|---|---|
| 4,919,659 | A | 4/1990 | Horbett |
| 5,304,398 | A | 4/1994 | Krusell |
| 5,451,428 | A | 9/1995 | Rupp |
| 6,232,458 | B1 | 5/2001 | Weiss |
| 6,335,029 | B1 * | 1/2002 | Kamath et al. ............... 424/423 |
| 6,627,397 | B1 * | 9/2003 | Nakamura et al. ........... 435/6.12 |
| 7,217,769 | B2 | 5/2007 | Zamora |
| 7,258,988 | B2 | 8/2007 | Yang |
| 7,311,970 | B2 | 12/2007 | Michal |
| 2004/0193177 | A1 | 9/2004 | Houghton |
| 2006/0121012 | A1 * | 6/2006 | Kutryk et al. ............. 424/93.21 |
| 2007/0281117 | A1 | 12/2007 | Kaplan |

FOREIGN PATENT DOCUMENTS

| | | |
|---|---|---|
| WO | 9414958 | 7/1994 |
| WO | 9834563 | 8/1998 |
| WO | 9903886 | 1/1999 |
| WO | 9945894 | 9/1999 |
| WO | 0050068 | 8/2000 |
| WO | 2006091775 | 8/2006 |
| WO | 2007048115 | 4/2007 |
| WO | 2007104107 | 9/2007 |
| WO | 2008037028 | 4/2008 |
| WO | 2009015420 | 2/2009 |

OTHER PUBLICATIONS

Kielty et al., "Applying elastic fibre biology in vascular tissue engineering", 2007, Phil. Trans. R. Soc. B, pp. 1293-1312.*

Tran et al. ,"Plasma Modification and Collagen Binding to PTFE Grafts", Journal of Colloid and Interface Science, 1989, pp. 373-381.*

Abraham and Carnes, "Isolation of a cross-linked dimer of elastin.", J. Biol. Chem., 253:7993-7995 (1978).

Bashir, et al., "Characterization of the complete human elastin gene. Delineation of unusual features in the 5'-flanking region.", J. Biol. Chem., 264:8887-8891 (1989).

Bilek, et al., "Functional attachment of horse radish peroxidase to plasma-treated surfaces", Smart Materials III, vol. 5648 (Ed, Wilson, A. R.) SPIE, pp. 62-67 (2004).

Bilek, et al., "Plasma-based ion implantation utilising a cathodic arc plasma", Surface and Coatings Technology, 156:136-142 (2002).

Buttafoco, et al., "Electrospinning of collagen and elastin for tissue engineering applications", Biomaterials, 27:724-734 (2006).

Cao, et al., "Glow discharge plasma treatment of polyethylene tubing with tetraglyme results in ultralow fibrinogen adsorption and greatly reduced platelet adhesion.", J. Biomed. Mater. Res. A, 79(4):788-803 (2006).

Clarke and Weiss, "Microfibril-associated glycoprotein-1 binding to tropoelastin: multiple binding sites and the role of divalent cations.", Eur. J. Biochem., 271:3085-3090 (2004).

Collins and Ferlauto, "Advances in plasma-enhanced chemical vapor deposition of silicon films at low temperatures", Curr. Opin. Solid State Mater. Sci., 6:425-437 (2002).

Erbel, et al., "Temporary scaffolding of coronary arteries with bioabsorbable magnesium stents: a prospective, non-randomised multicentre trial.", Lancet, 369:1869-1875 (2007).

Gan, et al. "Etching and structural changes in nitrogen plasma immersion ion implanted polystyrene films", Nuclear Instruments and Methods in Physics Research B, 247:254-260 (2006).

Gan, et al., "Comparison of protein surface attachment on untreated and plasma immersion ion implantation treated polystyrene: protein islands and carpet.", Langmuir, 23 (5):2741-2746 (2007).

Grabarek and Gergely "Zero-length crosslinking procedure with the use of active esters", Anal. Biochem., 185(1):131-135(1990).

Gunatillake, et al., "Poly(dimethylsiloxane)/poly(hexamethylene oxide) mixed macrodiol based polyurethane elastomers. I. Synthesis and properties", J. App. Poly. Sci., 76:2026-2040 (2000).

Hinds, et al., "Development of a reinforced porcine elastin composite vascular scaffold", J. Biomed. Mater. Res. Part A, 77:458-469 (2006).

Kaiser, et al., "Incremental cost-effectiveness of drug-eluting stents compared with a third-generation bare-metal stent in a real-world setting: randomised Basel Stent Kosten Effektivitäts Trial (BASKET).", Lancet, 366:921-929 (2005).

Kannan, et al., "Current status of prosthetic bypass grafts: a review", J. Biomed. Mater. Res. B Applied Biomaterials, 74:570-581(2005).

Li, et al., "Electrospun protein fibers as matrices for tissue engineering", Biomaterials, 26(30):5999-6008 (2005).

(Continued)

*Primary Examiner* — Karlheinz R Skowronek
*Assistant Examiner* — Lianko Garyu
(74) *Attorney, Agent, or Firm* — Pabst Patent Group LLP

(57) ABSTRACT

Biocompatible materials for use in vascular applications or for implantation have been engineered, combining human recombinant tropoelastin with other synthetic or natural biomaterials to form protoelastin. The materials can be in the form of elastin films on metal or polymer substrates, laminates of alternating polymer and elastin, blends of polymer and elastin, or elastin crosslinked with or tethered to polymer or metal. These are mechanically stable, elastic, strong and biocompatible (i.e., not thrombogenic and promoting adhesion of cells, especially human endothelial cells), not eliciting a foreign body response. Plasma polymerization of substrate is shown to enhance biocompatibility, especially when used to bind elastin or other protein to the substrate.

26 Claims, 11 Drawing Sheets

(56) References Cited

OTHER PUBLICATIONS

Lu, et al., "Improved endothelial cell adhesion and proliferation on patterned titanium surfaces with rationally designed, micrometer to nanometer features", Acta Biomater., 4 (1):192-210 (2008).

Ma, et al., "DLC coatings: effects of physical and chemical properties on biological response.", Biomaterials, 28(9):1620-1628 (2007).

Mueller, et al., "Surface engineering of stainless steel materials by covalent collagen immobilization to improve implant biocompatibility.", Biomaterials, 26 (34):6962-6972 (2005).

Nosworthy, et al., "The attachment of catalase and poly-l-lysine to plasma immersion ion implantation-treated polyethylene.", Acta Biomater., 3:695-704 (2007).

Ozaki, et al., "New stent technologies.", Prog. Cardiovasc. Dis., 39:129-140 (1996).

Phaneuf, et al., "Modification of polyethylene terephthalate (Dacron) via denier reduction: effects on material tensile strength, weight, and protein binding capabilities", J. Appl. Biomater., 6:289-299 (1995).

Pitt, et al., "Attachment of hyaluronan to metallic surfaces.", J. Biomed. Mater. Res. A, 68(1):95-106 (2004).

Plant, et al., "Behaviour of human endothelial cells on surface modified NiTi alloy.", Biomaterials, 26(26):5359-5367 (2005).

Prunotto and Galloni, "Stenting: biomaterials in mini-invasive cardiovascular applications.", Anal. Bioanal. Chem., 381(3):531-533 (2005).

Scott, "Restenosis following implantation of bare metal coronary stents: pathophysiology and pathways involved in the vascular response to injury.", Adv. Drug Deliv. Rev., 58 (3):358-376 (2006).

Singh and Dahotre, "Corrosion degradation and prevention by surface modification of biometallic materials.", J. Mater. Sci. Mater. Med., 18(5):725-751 (2007).

Steel, et al., "Nanosecond Responses of Proteins to Ultra-High Temperature Pulses", Biophys. J., 91(6):L66-68 (2006).

Stitzel, et al., "Controlled fabrication of a biological vascular substitute", Biomaterials, 27:1088-1094 (2006).

Teo and Ramakrishna "A review on electrospinning design and nanofibre assemblies", Nanotechnology, 17:R89-R106 (2006).

Teo, et al. "Porous tubular structures with controlled fibre orientation using a modified electrospinning method", Nanotechnology, 16:918-924 (2005).

Toonkool, et al., "Thermodynamic and hydrodynamic properties of human tropoelastin. Analytical ultracentrifuge and pulsed field-gradient spin-echo NMR studies.", J. Biol. Chem., 276:28042-28050 (2001).

Xue and Greisler, "Biomaterials in the development and future of vascular grafts", J. Vasc. Sur., 37:472-480 (2003).

Yin, et al., "Plasma polymer surfaces compatible with a CMOS process for direct covalent enzyme immobilization", Plasma Process. Polym., 6:68-75 (2008).

Yin, et al., "Covalent immobilization of tropoelastin on a plasma deposited interface for enhancement of endothelialisation on metal surfaces", Biomaterials, 30:1675-1681 (2009).

Yuan, et al., "Plasma polymerized n-butyl methacrylate coating with potential for re-endothelialization of intravascular stent devices", J. Mater Sci.:Mater Med., 19:2187-2196 (2008).

* cited by examiner

CHEMICALLY AND BIOLOGICALLY MODIFIED MEDICAL DEVICES

CROSS-REFERENCE TO RELATED APPLICATIONS

This application claims priority to and benefit of U.S. Provisional Patent Application No. 61/143,085 filed on Jan. 7, 2009, by Anthony Steven Weiss, Martin Kean Chong Ng, Steven Garry Wise and Anna Waterhouse, and where permissible is incorporated by reference in its entirety.

FIELD OF THE INVENTION

This application generally relates to the production of a biocompatible stent which encourages endothelialisation and discourages thrombosis, by covalently binding tropoelastin in a bioactive conformation to a metal or polymer surface.

BACKGROUND OF THE INVENTION

Coronary artery atherosclerosis disease (CAD) is the leading cause of death and disability in Western society and is expected to be the number one cause of death worldwide by 2020 ((Topol, et al., 2006 Hum. Mol. Genet., 15 Spec No 2:R117-23). It affects more than 11 million people in the United States alone. Occlusion of coronary vessels results in reduced blood flow to heart muscle, damage to this tissue and ultimately myocardial infarction (MI), of which there are over 1.5 million in the United States each year.

Treatment of CAD in the last two decades has progressively shifted from a predominantly surgical approach to the increasing use of percutaneously introduced therapies (Wong, et al., Metab Syndr Relat Disord. 2006 Winter; 4(4): 233-6. Percutaneous transluminal coronary balloon angioplasty (PTCA) involves the insertion of a balloon catheter into the peripheral circulation, which is threaded through the arterial system into the affected vessel. Inflation of the balloon expands the lumen of the diseased artery and pushes back obstructing plaques, effectively increasing the blood flow in this area. The therapy, however, does not usually result in a permanent opening of the affected coronary artery and can cause significant damage to the treated vessel.

A key problem associated with PTCA is the injury caused to the artery during inflation of the balloon and the corresponding hyperextension of the vessel wall. Following deflation and removal of the balloon, damaged portions of the arterial lining can occlude the vessel and thrombosis can develop as a result of damage to the endothelial cell lining. More commonly though, recoil and remodeling of the ballooned vessel triggers the hyper proliferation of smooth muscle cells leading to neointima formation and narrowing of the vessel lumen. This narrowing is commonly referred to restenosis (Scott, 2006 Adv. Drug Del.iv Rev., 58(3):358-76 (2006)). Two key clinical trials (BENESTENT, STRESS) in the early 1990s (Serruys, et al., N. Engl. J. Med., 331:489-95 (1994); Fischman, et al., N. Engl. J. Med., 331:496-501 (1994)) established the superiority of stent placement over PCTA alone. They concluded that the clinical and angiographic outcomes were better in patients who received a stent than in those who received standard coronary angioplasty and subsequent reintervention was required less often (Ozaki, et al., Prog. Cardiovasc. Dis., 39:129-40 (1996)). It was found that the use of coronary stents was effective at inhibiting both vessel recoil and remodeling, decreasing the frequency of restenosis by approximately 50% (Hoffman and Mintz, Eur. Heart Jour., 21:1739-49 (2000)). Stents are metal scaffolds, commonly stainless steel or an alloy such as cobalt-chromium and are usually cylindrical or tubular in shape. Their primary function is to hold open the treated artery following lumen expansion, preventing recoil and minimizing damage to the vessel. Stents can be crimped onto a catheter and balloon, such as in PCTA or be self expanding. By providing scaffolding upon expansion, stents are able to increase the size of the arterial lumen to a greater extent than PTCA by preventing arterial recoil following balloon dilatation.

While stents reduce the problem of vessel recoil, the excessive proliferation of smooth muscle cells remains problematic. Stents induce proliferation at both the luminal and tissue (mural) surfaces and trigger inflammation concentrated at the stent struts. The occurrence and extent of in-stent restenosis is correlated to the amount of physical damage to the endothelium and severity of the disruption to adventia and media vessel layers that occurs upon deployment (Toutouzas, et al., Eur. Heart Jour., 25:1679-89 (2004)).

Metal alloys are widely used in medicine, with stainless steel, titanium, cobalt-chromium and nitinol most commonly used (Singh and Dahotre, J. Mater. Sci.: Mater. Med., 18(5): 725-51 (2007)). In cardiovascular medicine metallic implants generally provide blood contacting surfaces such as those used in replacement heart valves, pacemaker components, hemodialysis membranes, and stents (Balasubramanian, et al., J. Biomater. Sci. Polymer Edn., 9(12):1349-59 (1998)). These materials provide favourable tensile properties, fatigue and corrosion resistance, but suffer from poor endothelial cell interactions and are profoundly thrombogenic (Hong, et al., Biomaterials, 26(26):5359-67 (2005)). The positive aspects of stent use are also counter balanced by the thrombogenic nature of stainless steel (and other stent materials) and thus the requirement for anti-platelet therapy. Despite the re-narrowing of stented vessels and the common need for reintervention, the use of stents has increased, such that by 1999 almost 85% of percutaneous coronary interventions involved their use (Serruys, et al., N. Engl. J. Med., 354:483-95 (2006)).

The most favoured approach to improving stent performance has been to coat the stents with various anti-thrombogenic or anti-proliferative agents in order to reduce thrombosis and restenosis. The two most successful anti-proliferative compounds used for drug eluting stent ("DES"), Sirolimus (and its limus variants) and Paclitaxel, interrupt smooth muscle cell proliferation and endothelialisation, preventing occlusion of the vessel caused by neointimal hyperplasia (Gershlick, Heart, 91 Suppl 3:24-31 (2005)). The drugs are generally delivered from nonerodible or erodible polymer layers covering the stent and can be released in a range of doses and rates. Both have been shown to be highly effective at reducing restenosis and re-intervention rates, when compared to bare metal stents. The overall rate of adverse cardiac events was also reduced, in the case of Sirolimus, by about 25%, due entirely to the increased revascularization achieved when using a DES (Moses, et al., N. Engl. J. Med., 349:1315-23 (2003); Morice, et al., N. Engl. J. Med., 346:1773-80 (2002)). Current trial data indicates that there are not significant differences in the performance of these two anti-proliferative agents, and both are equally effective (Brodie, Jour. Intervent. Cardiol., 19:39-42 (2006)).

Due to the high efficacy demonstrated for these compounds, the use of DES has markedly increased over the five years they have been available and are now in widespread use. Only recently have clinicians concluded long-term follow ups on patients receiving DES and some are signalling that not all the effects of DES are positive (Tsimikas, Jour. Amer. Coll. Cardiol., 47:2112-5 (2006)). Concerns regarding late stent thrombosis in DES were first raised in 2003/4 and are being perpetuated by longer term clinical studies in 2006.

One such recent study (BASKET-LATE) prospectively followed 746 consecutive patients who randomly received either DES or bare-metal stents in the Basel Stent Kosten-Effektivitats Trial (Kaiser, et al., *Lancet,* 366:921-9 (2005)) and who were event-free at the time their anti-platelet therapy (Clopidogrel) was stopped (six months). For BASKET-LATE, the patients were followed for an additional year beyond the six-month mark. Following the discontinuation of anti-platelet therapy, the rates of MI were higher in those patients receiving DES than those with bare-metal implants (4.9% vs 1.3%). DES was also associated with increased risk of death, possibly caused by late thrombosis formation (Pfisterer, et al., *Jour. Amer. Coll. Cardiol.,* 48:2584-91 (2006)).

Materials exhibiting true biocompatibility perform their function without eliciting an undue host response or resulting in adverse clinical outcomes (Williams, *Biomaterials,* 29(20):2941-53 (2008)). Further, truly biocompatible materials should facilitate beneficial cell and tissue interactions appropriate to the specific application. A key problem with respect to cell interactions of endovascular stents has been suboptimal endothelialisation. This is highlighted by drug-eluting coronary stents where delay and/or absence of stent endothelialisation, predisposes to late thrombotic events with adverse clinical consequences (Pfisterer, et al., *Jour. Amer. Coll. Cardiol.,* 48:2584-91 (2006)).

Efforts to enhance the biocompatibility of metal surfaces have involved a number of diverse approaches. Heat treatment (Plant, et al., *Biomaterials,* 26(26):5359-67 (2005)), surface oxidation (passivation) (Prunotto and Galloni, *Anal. Bioanal. Chem.,* 381(3):531-3 (2005)), nano-scale patterning (Lu, et al., *Acta Biomater.,* 4(1):192-210 (2008)) and carbon coatings (Ma, et al., *Biomaterials,* 28(9):1620-8 (2007)) have shown some improvements in compatibility in vitro. Coating metallic implants with bioactive molecules such as collagen (Muller, et al., *Biomaterials,* 26(34):6962-72 (2005)) and hyaluronan (Pitt, et al., *J. Biomed. Mater. Res. A,* 68(1):95-106 (2004)) has also improved cellular attachment and proliferation, though robustly adhering biomolecules to metal interfaces is not a trivial task. A common limitation to the clinical translation of materials functionalised with biomolecules is that the coatings are not robust enough to withstand in vivo exposure.

The requirements of a vascular device surface for immobilising proteins include high protein binding capacity, the ability to retain the protein activity and ultimately high biocompatibility. Proteins interact with metal alloys through non-specific, Van der Waals type interactions, resulting in protein-substrate association of variable strength. Proteins bound to a metallic surface in this way are often susceptible to removal by physical forces (e.g. by washing) and to unfolding and loss of activity. For medical applications, any bioactive coating requires a strong mechanism of attachment to create a surface robust enough to withstand in viva exposure, in this case, blood flow. Covalent immobilisation is usually preferred for this reason. A common approach is to construct a functional or biologically active thin film tethered to a supporting substrate. The biologically active molecules can be held in place by incorporation in Langmuir-Blodgett multi-layers (Kahlert and Reiser, *Cell Calcium,* 36(3-4):295-302 (2004)), or on plasma treated polymeric surfaces (Gan, et al., *Langmuir,* 23(5):274'-6 (2007)) for example. Such methods however are usually not suitable for use with the metallic surfaces prevalent in cardiovascular applications.

The ability to covalently immobilise proteins onto metals is of interest for cardiovascular medicine as it enables the therapeutic modulation of the vascular biological properties of a large range of cardiovascular devices such as coronary stents. The immobilisation of a biomolecule requires reliable attachment and sufficient density to allow it to interact preferentially with cells and blood.

It is therefore an object of the present invention to provide materials which are suitable for vascular application that are biocompatible and not thrombogenic or have very low thrombogenicity.

It is a further object of the present invention to provide such materials which can withstand physiological stent conditions, including deployment, flow etc.

SUMMARY OF THE INVENTION

Biocompatible materials suitable for use in medical devices such as stents, especially for use in vascular applications, or for implantation or insertion into lumens such as those from the bladder, orthopedics, tissue engineering matrices or prosthetics, have been engineered, combining a protein, most preferably full length human recombinant tropoelastin, protoelastin, or elastin (jointly referred to as elastin unless otherwise specified), with other synthetic or natural biomaterials. The materials can be in the form of elastin films on metal, ceramic, carbon, or polymer substrates, laminates of alternating polymer and elastin, blends of polymer and elastin, or elastin crosslinked with or tethered to polymer or metal. These biomaterials can be or include other extracellular matrix materials such as fibrillins, crosslinked glycosaminoglycans ("GAGs"), collagen and collagen derivatives, and other natural materials, which may in some cases be the polymer substrate or blend, and drugs or other bioactive agents.

In a preferred embodiment, the engineered materials form a stent which has reduced thrombogenicity and increased endothelialisation due to coating the surface with protoelastin. In the most preferred embodiment, the elastin is covalently attached to a metal surface using a technique that retains the elastin in a conformation that encourages endothelial cell interactions in in vitro studies. This also allows any combination of one or more other biomolecules to be immobilised on any non-polymer substrate. Plasma polymerization of substrate is shown to enhance biocompatibility, especially when used to bind elastin or other extracellular matrix materials to the substrate. The flexibility in engineering and design makes elastin biomaterials suited not only to the production of conduits but any number of other vascular applications that require blood contacting surfaces. Elastin, tropoelastin and the subsequently engineered biomaterial protoelastin provide the opportunity to satisfy a large unmet need for a biocompatible material adaptable enough to meet a range of diverse vascular uses. These are mechanically stable, elastic, strong and biocompatible (i.e., not thrombogenic and promoting adhesion of cells, especially human endothelial cells, and not eliciting a foreign body response).

DETAILED DESCRIPTION OF THE INVENTION

I. Definitions

Figure 1A:
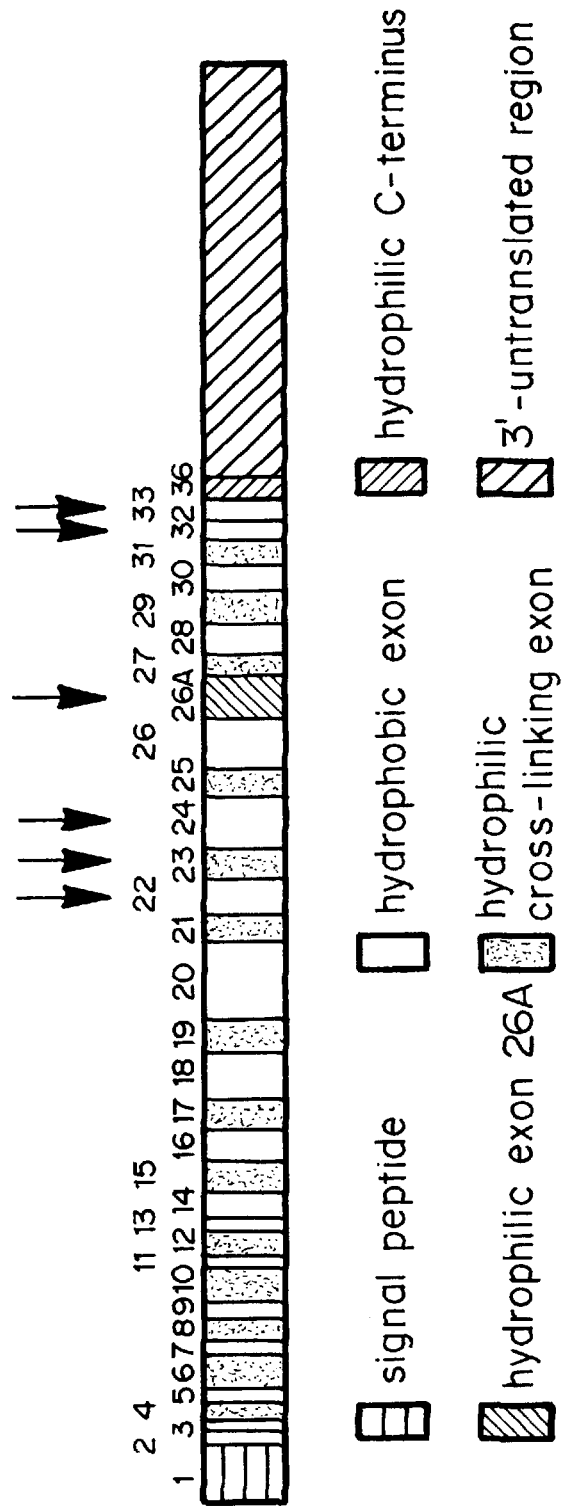
FIG. 1A is a schematic of the arrangement of exons in the human elastin gene. The figure highlights the alternating hydrophobic and hydrophilic exons that characterize much of the structure. Domains 26A and 26 are not easily characterized and are separately noted. Exons subject to alternate splicing, giving rise to multiple tropoelastin isoforms, are marked with an arrow. Figure from Vrhovski and Weiss, *Eur. J. Biochem.,* 258(1): 1-18 (1998)).

As used herein, the term "tropoelastin" refers to the protein that is expressed and post-translationally modified from the gene encoding elastin, prior to cross-linking to form elastin.

As used herein, the term "protoelastin" is recombinant human tropoelastin (and variations on this sequence), including alternative splicing constructs and insertion/deletions and mutants based on the human elastin sequence, either cross-linked or uncross-linked, which is engineered for use as a biomaterial.

As used herein, the term "thrombogenicity" refers to the tendency of a material in contact with blood to produce a thrombus, or clot. All surfaces will be thrombogenic, given low enough flow rates and high enough viscosity, though some perform better than others. Existing vascular materials like stainless steel, Dacron and ePTFE are all considered to be pro-thrombogenic. Both collagen and fibronectin are also highly thrombogenic, while trials of the protoelastin described herein show it to be no more thrombogenic than saline.

As used herein, the term "endothelialization" refers to the attachment and proliferation of endothelial cells on the surface of the substrate material. The luminal surface of the vasculature is covered by a layer of endothelial cells, which mediate blood interactions and modulate the proliferation of other cell types like smooth muscle cells. The endothelial cell lining is easily damaged and this is known to occur during stent deployment, or bypass grafting of autologous vessels. This damage can lead to a host of negative performance consequences such as neointimal hyperplasia and clot formation. Currently available commercial synthetic vascular materials have no endothelial cells when implanted and rely on host cells attaching and proliferating. The literature generally indicates that the faster a functioning endothelial cell layer can be recruited, the better the vascular material will perform.

As described in U.S. Pat. No. 7,258,988, the vascular endothelium forms a "container" for blood. As long as this cellular layer remains intact and is functioning normally, a non-thrombogenic surface is presented to the circulating blood, allowing it to remain fluid and perform its nutritive functions unimpeded by intravascular clotting. Physical disruption of the endothelial lining, even on a microscopic scale, elicits an immediate hemostatic response, involving localized activation of the coagulation cascade and the adherence and aggregation of platelets, an adaptive reaction that serves to limit blood loss at sites of injury.

As used herein, the term "mechanically stable" refers to the ability of the coating of protoelastin to remain tethered to the metal substrate (via the acetylene intermediary) and biologically active to encourage endothelialisation.

II. Materials

As described below, it has been discovered that plasma polymerization of a substrate can greatly enhance biocompatibility, which is further enhanced by coupling of proteins such as elastin, collagen or other extracellular matrix materials. The protein, alone or in combination with other synthetic or natural biomaterials, can be used to impart the desired mechanical and biological properties. In some of the preferred embodiments, elastin is blended with polymer; in other embodiments, the elastin is formed into a laminate with films or layers of polymer. In other embodiments, elastin is used as a coating for existing implantable materials. For example, the device can be a stent coated with protoelastin. The device is less thrombogenic, encourages endothelialisation, and reduces neointima formation because of this coating. To achieve this, the protein coating has to be robust enough to withstand deployment and blood flow and also present the protein in a biologically active conformation.

The protoelastin is covalently bound to metal substrates via a polymer intermediary such as acetylyene (ethylene). The acetylene layer is blended with the metal surface using plasma polymerisation, converting the inert metal surface into a reactive polymer surface. The composition of the polymer layer can be widely varied and conditions for optimal protein binding and activity were chosen. Similar results can be achieved using other carbon chains (such as hexane) or different plasma conditions.

Given the current problems with regards to late stent thrombosis in drug eluting stents, many groups are exploring the use of biodegradable coatings for drug release. In such instances, a biodegradable drug release coating may be applied over a biocompatible coating such as protoelastin covalently bound by plasma polymerization. This would allow local elution of a drug, leaving behind a stent with a biocompatible coating.

Stents can also be manufactured from degradable materials as alternatives to permanent metallic scaffolds. These bioresorbable stents have commonly been manufactured from polymers such as poly-lactic acid and polyglycolic acid, which remain in the body for 6-24 months (Zilberman and Eberhard, *Ann. Rev. Biomed. Eng.,* 8:153-180 (2006)). Bioresorbable stents can also be made from metal alloys such as magnesium. These are completely resorbed within 2 months and have shown promising clinical outcomes (Erbel, Di Mario, et al., *Lancet,* 369:1869-75 (2007)). Plasma polymerisation and/or coating with protoelastin is also relevant to the improvement of the short term biocompatibility of these temporary scaffolds and could easily be adapted for their modification.

A. Elastin

Elastin is an extracellular matrix protein that is found within skin, lungs, bladder, elastic cartilage and arteries. Elastin is an insoluble polymer that is assembled extracellularly and is composed of monomer tropoelastin molecules. Elastin is principally synthesized during the development or growth of tissues, with tropoelastin expression occurring during mid- to late fetal or embryonic periods.

1. Tropoelastin

Figure 1B:
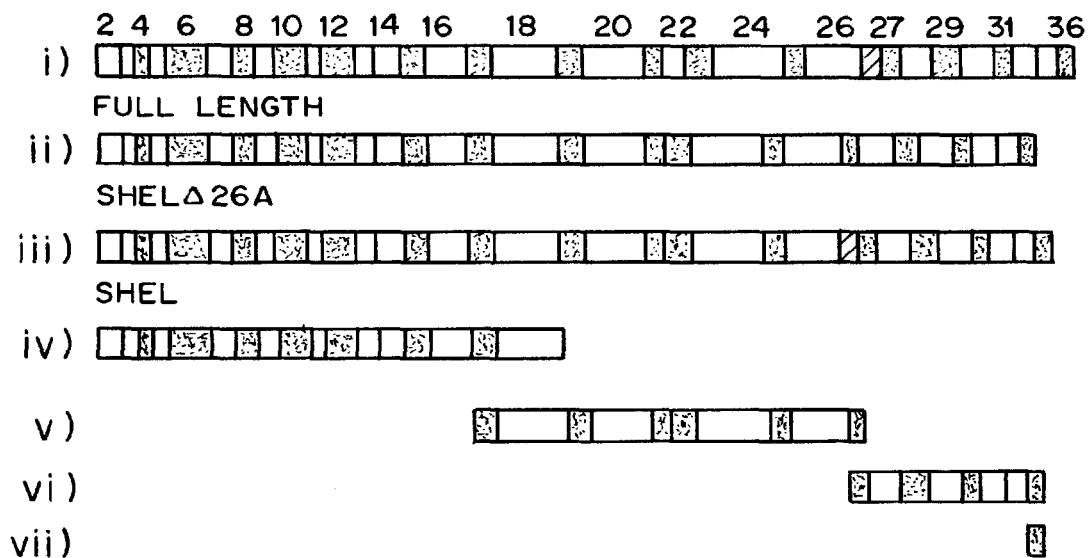
FIG. 1B is a schematic representation of common tropoelastin splice forms and derivatives. Hydrophilic exons are shaded, domain 26A is striped. (i) all possible domains expressed by the elastin gene; (ii) a common isoform, lacking domains 22 and 26A; (iii) a common isoform lacking domain 22, but including 26A; (iv) construct encompassing the N-terminus; (v) construct encompassing the center of elastin; (vi) construct encompassing the C-terminus; and (vii) construct encompassing domain 36.
Figure 1C:
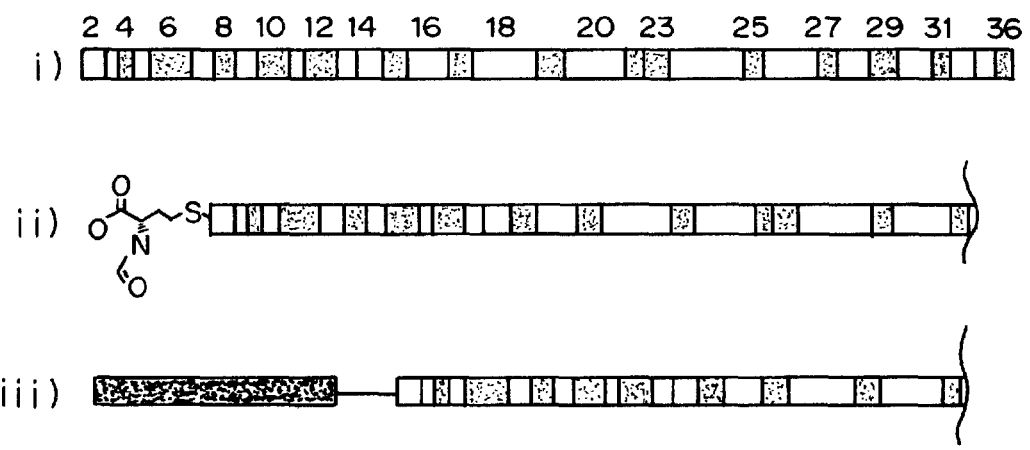
FIG. 1C is a schematic of possible modifications to recombinant tropoelastin. (i) a frequently expressed isoform; (ii) formyl methionine modification of the N-terminus; and (iii) N-terminal tag (short peptide as his-tag) modification.

Tropoelastin is encoded by a single-copy gene including 36 domains, as shown in FIG. 1A. Domain 1 is a signal peptide. Domains 2, 3, 5, 7, 9, 11, 13, 14, 16, 18, 20, 22, 24, 26, 28, 30, 32 and 33 are hydrophobic domains; domains 4, 6, 8, 10, 12, 15, 17, 19, 21, 23, 25, 27, 29, and 31 are hydrophilic crosslinking exons; domain 26A is a hydrophilic exon; domain 36 is the hydrophilic C-terminus. Domains 26A and 36 are not easily characterized. Exons 22, 23, 24, 26A, 32 and 33 are subject to alternative splicing, giving rise to multiple tropoelastin isoforms. Alternative splicing of tropoelastin mRNA transcripts results in various tropoelastin isoforms. Representative tropoelastin splice forms and derivatives are shown in FIG. 1B. (i) is the tropoelastin including all possible domains expressed by the elastin gene; (ii) is a common isoform lacking domains 22 and 26A; (iii) is a common isoform lacking domain 22, but including 26A; (iv) is a construct encompassing the N-terminus; (v) is a construct encompassing the center; (vi) is a construct encompassing the C-terminus; and (vii) is a construct encompassing domain 36. FIG. 1C is a schematic of common derivatives of tropoelastin: (i) a frequently expressed isoform; (ii) formyl methionine modification of the N-terminus; and (iii) N-terminal tag such as His-tag.

Human tropoelastin is synthesized as an approximately 72,000 Da protein by a variety of cells including smooth muscle cells, endothelial cells, fibroblasts and chondrocytes. Secretion is followed by an orchestrated interplay of macromolecular partners that assist in delivering tropoelastin monomers to sites of elastogenesis. Such interactions facilitate identification of sites for elastin assembly through associating microfibrillar proteins and encourage deposition with previously accreted tropoelastin. Tropoelastin is encoded by a single gene that possesses 36 exons and gives rise to multiple isoforms. In human tropoelastin the mRNA encodes a 72,000 Da polypeptide which undergoes splicing and removal of signal peptide, leaving a mature protein with a molecular weight ranging from 60,000 Da to 70,000 Da (Visconti, et al., *Matrix Biol,* 22:109-21 (2003)). Domains 22, 23, 24, 26A, 30, 32 and 33 undergo developmentally regulated alternative splicing (Bashir, et al., *J Biol Chem,* 264:8887-91 (1989)), resulting in these multiple isoforms (Parks and Deak, *Am J Respir Cell Mol Biol,* 2:399-406 (1990)). One skilled in the art will appreciate that these isoforms behave similarly for the purposes of their use as a biomaterial. These can be modified by substituting, adding, or deleting one or more amino acids within these domains, or one or more domains.

Preferred tropoelastin splice variants include fragments encompassing roughly the first third of the molecule (called N18), the middle third (called 17-27) and the C-terminal third (called 27-C). This also extends to individual domains and short peptides suspected to be important to cell recognition, such as domain 36.

In a preferred embodiment, the variants are R515A (protease resistant) and/or M155n (lacking C-terminus). Both of these variants bind endothelial cells while maintaining the non-thrombogenicity of PPS, thereby demonstrating that the C-terminus is not essential, at least with respect to HUVECs. R515A is an arginine to alanine point mutation at the 515 position of SHELD26A designed to increase resistance to proteolytic cleavage. The M155n mutant is referenced in Clarke and Weiss Eur. J. Biochem. 271, 3085-3090 (2004).

Domain 36, the C-terminus of tropoelastin, is known to be highly conserved (greater than 78%) across species and contains two characteristic features which may impart some conformational preference. Two cysteine residues are found in domain 36 and form a disulfide bond, while the protein terminates with the positively charged RKRK (SEQ ID NO:1) sequence. Integrin binding in this region (Rodgers and Weiss, *Biochimie*, 86:173-178 (2004)) and evidence of interaction with glycosaminoglycans that mediate cell adhesion (Broekelmann, et al., *J Biol Chem.*, 280(49):40939-47 (2005)) are further indications of the importance of the conserved C-terminus.

2. Conversion of Tropoelastin to Elastin

Elastin is an extremely durable and insoluble biopolymer and is formed through the lysine-mediated cross-linking of its soluble precursor tropoelastin. In vivo, tropoelastin is secreted into the extracellular space and is quickly cross-linked by the action of an enzyme called lysyl oxidase. Complex, permanent covalent cross-links are formed. Conversion to elastin occurs in vivo by the action of lysyl oxidase, which converts the epsilon amine on side chains of occasional lysines in tropoelastin to the adipic semi-aldehyde. Coacervation juxtaposes modified and unmodified lysines to facilitate irreversible covalent cross-linking.

3. Purification of Elastin

Historically, elastin and tropoelastin have been difficult to isolate. Both can be harvested from a variety of animal sources including bovine, porcine and equine, preferably from elastin rich tissue such as ligament and aorta, Elastin is extracted from these tissue using harsh conditions including refluxing in ethanol, autoclaving, acid and trypsin digestion and sodium hydroxide. These conditions strip away fats and other matrix proteins like collagen, but also damage the elastin.

Obtaining the protein monomer precursor of elastin (tropoelastin) in large quantities remains difficult, with the monomer cross-linked into elastin before it can be harvested. Initially, isolation relied on animal hosts, usually pigs, with a copper deficient diet (Mecham and Foster, *Biochimica et Biophysica Acta*, 577:147-58 (1979)), deactivating the enzymes cross-linking function and perturbing elastic fiber assembly. The time and effort involved in this procedure was certainly not reflected in the average yield of 0.1% tropoelastin to aortic weight (Sandberg and Walt, *Methods in Enzymology*, 82 Pt A:657-65 (1982)). The method evolved marginally to introduce an enzyme inhibitor (Rich and Foster, *Biochem J*, 217:581-4 (1984)) and chicks (Abraham and Carnes, *J Biol Chem*, 253:7993-5 (1978)), but remained inefficient. As an alternative to tropoelastin, some researchers artificially make 'soluble elastin' by chemically treating elastin samples. Both ☐-elastin (Cox et al., *Biochim Biophys Acta*, 317:209-13 (1973)), an oxalic acid derivative of elastin, and κ-elastin, solubilized with potassium hydroxide have been investigated. Investigations with these systems continue to the present, while it is recognized that chemically degraded elastin cannot precisely represent the in vivo monomer (Starcher, et al., *Biochim Biophys Acta*, 310:481-6 (1973)). 'Soluble elastin' the soluble product of acid or base digestion of animal derived elastin is commercially available and the most commonly used variant in the literature.

4. Recombinant Tropoelastin

Recombinant tropoelastin was first expressed as a fusion protein in an *E. coli* bacterial system some 17 years ago (Indik et al., *Arch Biochem Biophys*, 280:80-6 (1990)). The HPLC purified protein exhibited an amino acid composition and size (72 kDa) anticipated for the full length clone used. The high purity of the recombinant protein produced in this system was beneficial, while persistent smaller fragments and the limitation of small yields were problematic, with only 2-4 mg produced per liter of culture. Soon after, a recombinant 60 kDa mature form of tropoelastin (Martin et al., *Gene*, 154: 159-66 (1995)) was expressed, following significant improvements to the bacterial expression system. This system boasts significantly higher yields of protein. Tropoelastin is now produced in gram quantities in a highly reproducible manner. Other groups have been involved in recombinant tropoelastin production, but none can produce it in comparable high yields and high purity.

This recombinant protein is recognized by cells to form elastin (Stone, et al., *Amer. J. Respir. Cell. Mol. Biol.*, 24:733-739 (2001)), associates at 37° C. (Toonkool, et al., *J. Biol. Chem.*, 276:28042-50 (2001)) and can be cross-linked chemically to form an elastin-like material (Mithieux, et al, *Adv. Protein Chemistry*, 70:437-61 (2004)). While this system can produce large quantities of high purity protein, monomer can be expressed in other recombinant systems or chemically synthesized.

Recombinant human elastin behaves very differently from elastin sourced from animals, the most common type discussed in the prior art. Biocompatibility and elasticity are intrinsic properties of endogenous elastin as demonstrated by its crucial role in aortic function. It mediates interactions with endothelial cells and provides recoil and, in combination with collagen, strength. Recombinant tropoelastin is preferably expressed in the *E. coli* expression system described in U.S. Pat. No. 6,232,458. U.S. Pat. No. 6,232,458 is directed to a method of recombinantly producing large scale quantities of human tropoelastin in a bacterial system.

5. Protoelastin

Protoelastin, as used herein, is a material that incorporates tropoelastin. The material is engineered to have desirable properties for a particular use. For example, the protoelastin may be engineered for human clinical vascular applications. The acetylene/metal interface has strength >15 MPa. The protein is covalently bound and resistant to SDS (detergent) washing.

Typically, increased strength is obtained through the selection of the other components of the composition and chemical modification, such as cross-linking of the recombinant human tropoelastin. Protoelastin, in the preferred embodiment, displays physical and structural properties similar to those of naturally occurring elastin including similar compliance and favorable cellular interactions (Mithieux and Weiss, *Adv. Protein Chem.*, 70:437-61 (2005)). These properties also can be manipulated by changing protein concentration, cross-linker type and polymerization conditions to engineer a material to suit a range of vascular biomaterial applications.

B. Polymeric Materials, Substrates and Laminates

Materials which can be plasma polymerized include metals, polymers, carbon, and ceramic. The protein, such as tropoelastin, can be applied to, crosslinked with, tethered to, blended with, or laminated as part of, one or more materials to form a surface, component, or device. In the preferred embodiment, a graded polymer such as acetylene layer is deposited on the surface of a metal, such that the initial deposition is metal, with increasing polymer, finishing with 100% polymer. The effect of this graded layer is that there is no defined metal/polymer interface and no resultant peeling off of the coating. The polymer layer is chemically activated using treatment with gas plasma, pre-disposing it to form covalent bonds with proteins. Immersion of the plasma polymerised surface in a protein solution is sufficient for covalent attachment, with no separate cross-linking agent required. Importantly, bioactivity is retained.

In another embodiment the plasma polymerised surface alone, in the absence of any protein coating, forms the surface of the device. The activated polymer surface has reduced thrombogenicity compared to the underlying metal substrate, though interactions with endothelial cells are not improved. A plasma polymerised surface alone is of particular use for applications that do not rely on endothelialisation for efficacy, such as heart valves.

1. Films, Coatings and Laminates

The tropoelastin can be applied to ceramic, bone, metal, carbon or polymer substrates to provide a biocompatible elastic surface. Typical metals include stainless steel and titanium. In one embodiment, the material is or includes one or more biodegradable or non-biodegradable synthetic polymers such as polylactides, polyglycolic acids, polycaprolactones, polycaprolactams, polyhexamethylene adipamide, polycarbonates, polyamides, polyanhydrides, polyamino acids, polyesters, polyacetals, polycyanoacrylates, polyvinyl alcohols, polyvinyl chlorides, polyethylenes, polyurethanes, polypropylenes, polyacrylates, polystyrenes, polyvinyl oxides, polyvinyl fluorides, poly(vinyl imidazoles), polyethylene oxides, polytetrafluoroethylenes, silicone polymers and copolymers and combinations thereof. In another embodiment, the material is or includes one or more natural materials such as a protein, sugar or polysaccharide, or combination thereof. Representative examples include collagen, preferably type 1 and/or type 3, fibrin, gelatin, vitronectin, fibronectin, laminin, hyaluronic acid, glycosaminoglycans, their derivatives and mixtures thereof. Preferred glycosaminoglycans include chondroitin sulfate, dermatan sulfate, keratan sulfate, heparan sulfate, heparin and hyaluronan.

As demonstrated in the examples, it is critical to tether or crosslink the tropoelastin to the substrate, thereby forming a protoelastin material. Tethering is required to avoid the elastin from being removed by the shear forces associated with the passage of blood through the blood vessel and graft.

As used herein, a film or coating will typically be in the range of a few microns in thickness, or less. In a preferred embodiment, the coating consists primarily of protoelastin that promotes endothelial cell growth on a surface.

Figure 2:
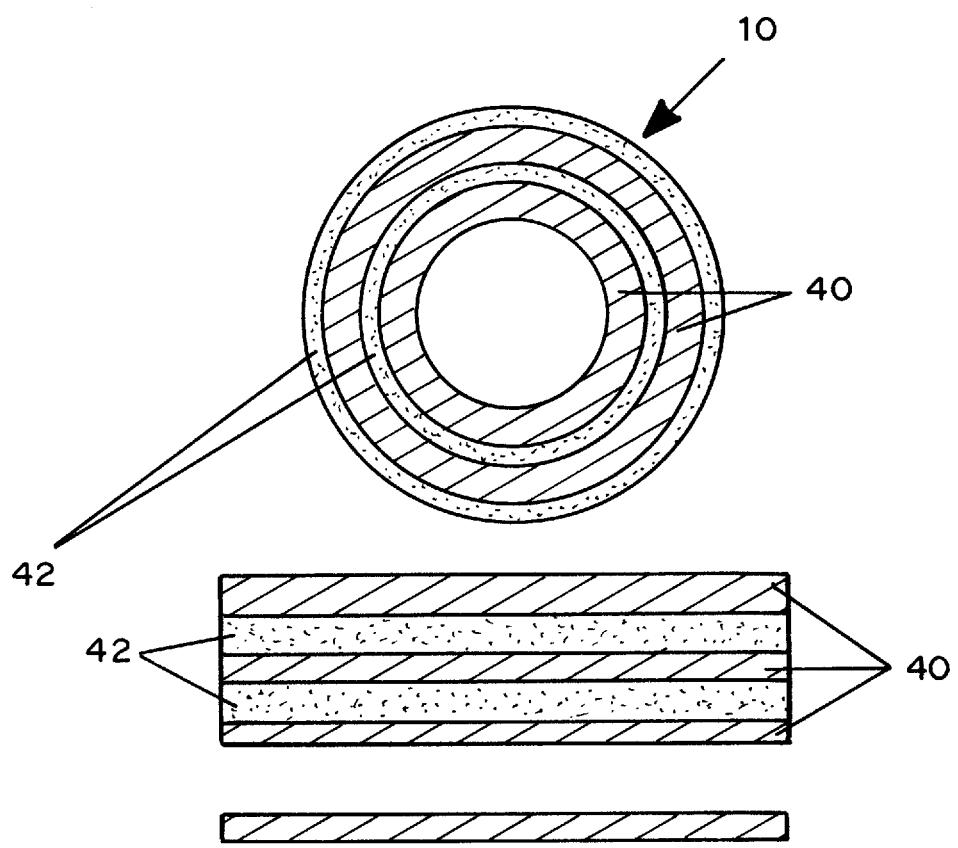
FIG. 2 is a prospective view of a tube and a cross-sectional view of a protoelastin-copolymer laminate, with the protoelastin on the luminal surface.
Figure 3:
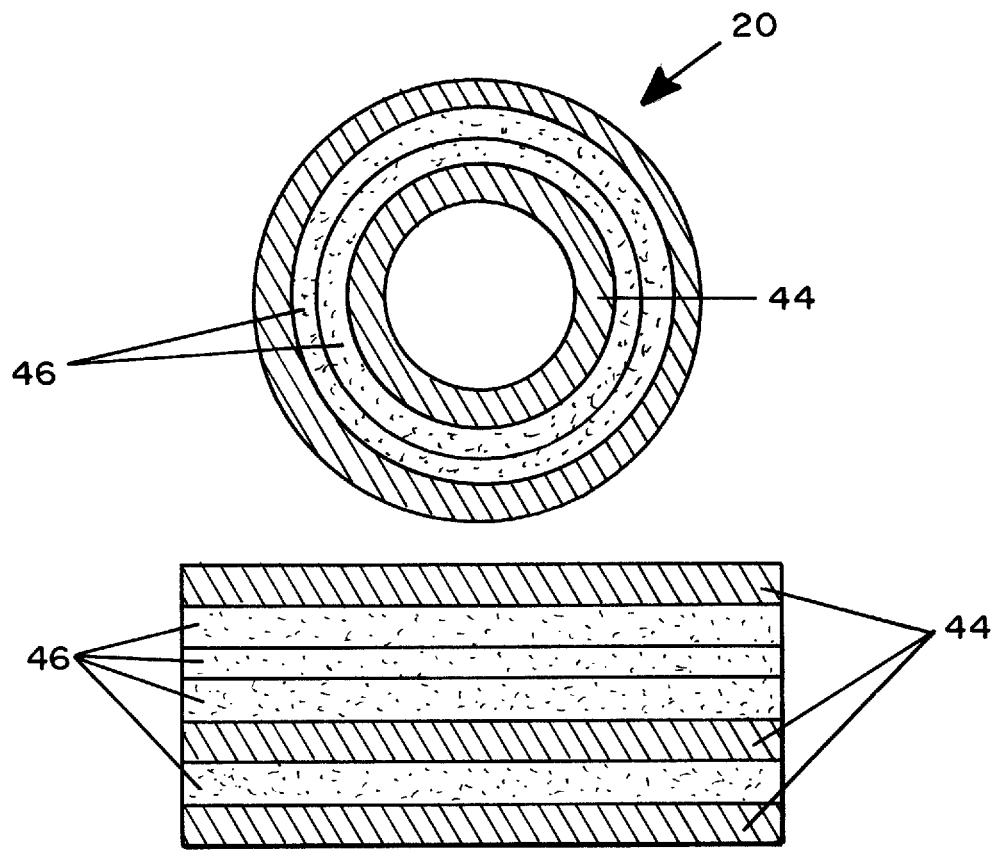
FIG. 3 is a prospective view of a tube and a cross-sectional view of a non-alternating copolymer laminate, with the protoelastin on the luminal surface.
Figure 4:
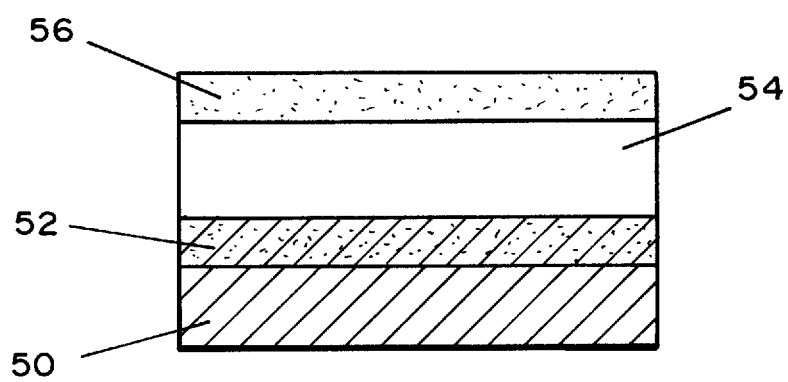
FIG. 4 is a schematic of a metallic substrate with a graded transition to an activated upper polymer layer, such as embedded acetylene, hexane or other carbon-containing chemical, using standard technologies. This upper layer is activated by plasma treatment to facilitate protein attachment. Protoelastin is obtained by covalent attachment of protein to this upper layer by immersion in a solution of tropoelastin or tropoelastin derivatives.

FIGS. 2-4 exemplify some of the protoelastin biomaterials. FIG. 2 is a schematic of a tube 10 formed of protoelastin layers 40, alternated with polymer layers 42. A tube formed solely of tropoelastin, even cross-linked tropoelastin, does not have the mechanical properties necessary for use in vascular applications.

In a preferred embodiment as described herein, shown in FIG. 3, tube 20 is a polymeric graft having a crosslinked tropoelastin layer 44 tethered on the inside luminal surface. Layers of tropoelastin 44 alternate with one or more layers of polymer 46.

FIG. 4 is a schematic of metallic substrate 50 with a graded transition 52 to an activated upper polymer layer 54 (such as embedded acetylene, hexane or other carbon-containing chemical) using standard technologies. This upper layer 54 is activated by plasma treatment to facilitate protein attachment. Protoelastin 56 is obtained by covalent attachment of protein to this upper layer by immersion in a solution of tropoelastin or tropoelastin derivatives.

2. Polymeric Blends

The material properties of the protoelastin can be modified by blending the tropoelastin with one or more other polymeric materials. The properties can be further modified through crosslinking and/or covalent coupling.

In one embodiment, the material is or includes one or more biodegradable or non-biodegradable synthetic polymers such as polylactides, polyglycolic acids, polycaprolactones, polycaprolactams, polyhexamethylene adipamide, polycarbonates, polyamides, polyanhydrides, polyamino acids, polyesters, polyacetals, polycyanoacrylates, polyvinyl alcohols, polyvinyl chlorides, polyethylenes, polyurethanes, polypropylenes, polyacrylates, polystyrenes, polyvinyl oxides, polyvinyl fluorides, polyvinyl imidazoles), polyethylene oxides, polytetrafluoroethylenes, silicone polymers and copolymers and combinations thereof. The protoelastin can include more than one polymer component.

In another embodiment, the material is or includes one or more natural materials such as a protein, sugar or polysaccharide, or combination thereof. Representative examples include collagen, preferably type 1 and/or type 3, fibrin, gelatin, vitronectin, fibronectin, laminin, hyaluronic acid, proteoglycans, glycosaminoglycans, their derivatives and mixtures thereof. Preferred glycosaminoglycans include chondroitin sulfate, dermatan sulfate, keratan sulfate, heparan sulfate, heparin and hyaluronan.

C. Additional Materials

The protoelastin materials can be used for drug delivery, incorporating a therapeutic, prophylactic or diagnostic agent, or incorporate materials such as growth factors which facilitate attachment and proliferation of one or more cell types.

Preferred therapeutic agents which may be delivered include:

Growth Factors: vascular endothelial growth factor, fibroblast growth factor, hepatocyte growth factor, connective tissue growth factor, placenta-derived growth factor, angiopoietin-1 and granulocyte-macrophage colony-stimulating factor.

Agents modulating cellular behavior in relation to bioprosthesis: Vitronectin, hyaluronic acid, chondroitin sulfate, dermatan sulfate, keratan sulfate, heparan sulfate, heparin and hyaluronan. Laminin, small leucine rich repeat proteoglycans (SLRP) (e.g. decorin, byglycan, fibromodulin, lumican, ketatocan), perlecan, versican, fibulin, fibrillin, collagen I, collagen III, collagen IV, microfibrillar collagen, fibronectin, microfibrillar associated glycoproteins (MAGP), nidogen/entactin, agrin, dystroglycan, cadherins, angiostatin, enodstatin, tumstatin, canstatin, arrestin, restin, vastatin, endorepellin, cartilage oligomeric matrix protein (COMP), matrillin, fibrin gels, synthetic Arg-Gly-Asp (ROD) adhesion peptides, tenascins, Del-1, CCN family (e.g. Cyr61) hypoxia-inducible factor-1, acetyl choline receptor agonists and monocyte chemoattractant proteins.

Gene delivery agents: viral vectors for gene delivery (adenoviruses, retroviruses, lentiviruses, adeno-associated viruses) and non-viral gene delivery agents/methods (e.g. polycation polyethylene imine, functional polycations consisting of cationic polymers with cyclodextrin rings or DNA within crosslinked hydrogel microparticles, etc.).

Agents modulating cell replication/proliferation: target of rapamycin (TOR) inhibitors (including sirolimus, everolimus and ABT-578), paclitaxel and antineoplastic agents (including alkylating agents, e.g. cyclophosphamide, mechlorethamine, chlorambucil, melphalan, carmustine, lomustine, Ifosfamide, procarbazine, dacarbazine, temozolomide, altretamine, cisplatin, carboplatin and oxaliplatin), antitumor antibiotics (bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase), antimitotic agents (vincristine, vinblastine, vinorelbine, docetaxel, estramustine) and molecularly targeted agents (imatinib, tretinoin, bexarotene, bevacizumab, gemtuzumab ogomicin and denileukin diftitox))

Steroids: Corticosteroids, estrogens, androgens, progestogens and adrenal androgens Antiplatelet, antithrombotic and fibrinolytic agents: glycoprotein IIb/IIIa inhibitors, direct thrombin inhibitors, heparins, low molecular weight heparins, platelet adenosine diphosphate (ADP) receptor inhibitors, fibrinolytic agents (streptokinase, urokinase, recombinant tissue plasminogen activator, reteplase and tenecteplase etc).

Gene targeting molecules: small interference (si) RNA, micro RNAs, DNAzymes and antisense oligonucleotides Cells: progenitor cells (endothelial progenitor cells, CD34+, CD133+, KM+ or VCAM-1+ monocytes, hemopoietic stem cells, mesenchymal stem cells, embryonic stem cells) and differentiated cells (endothelial cells, fibroblasts and smooth muscle cells)

Drug delivery agents: mucoadhesive polymers (e.g. thiolated polymers)

Pharmacologic agents of local treatment of atherosclerosis: high density lipoprotein cholesterol (HDL), HDL mimetics and hydroxymethylglutaryl CoA (HMG-CoA) reductase inhibitors.

III. Methods of Manufacture of Materials and Devices

A. Biomedical Devices and Applications

The manufacture of the tropoelastin and protoelastin is discussed above.

These materials are then applied to or formed into material which forms, in whole or in part, a material for biomedical use. The application will determine the selection and design of the mechanical properties. The material can be applied as a part of a variety of clinical vascular applications including a vascular conduit, a stent, a stent-graft, a surgically or percutaneously implantable heart valve, a vascular/septal occlusion device, a vascular closure device or as a surface coating for a vascular device/application.

Figure 5A:
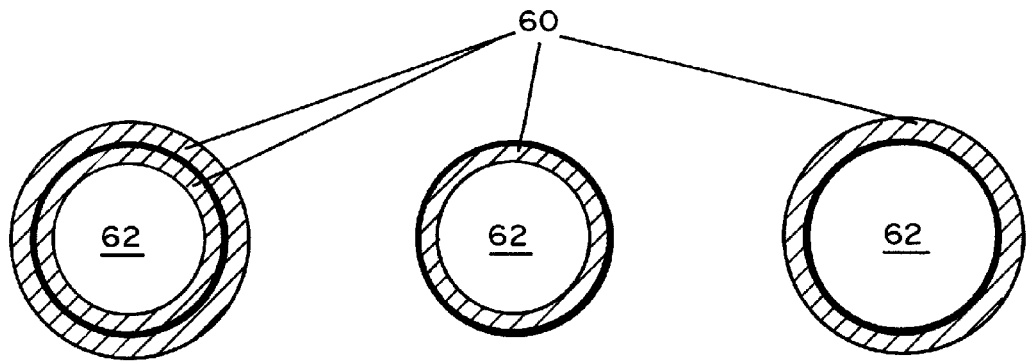
FIG. 5A is a schematic representation of side specific plasma polymerisation of a stent. Stent is represented in black in each ease. Plasma polymerisation treatment is represented in grey. Schematic shows plasma polymerisation treatment on (a) both sides, b) the luminal side only and c) the mural (ablumnial) side only.
Figure 5B:
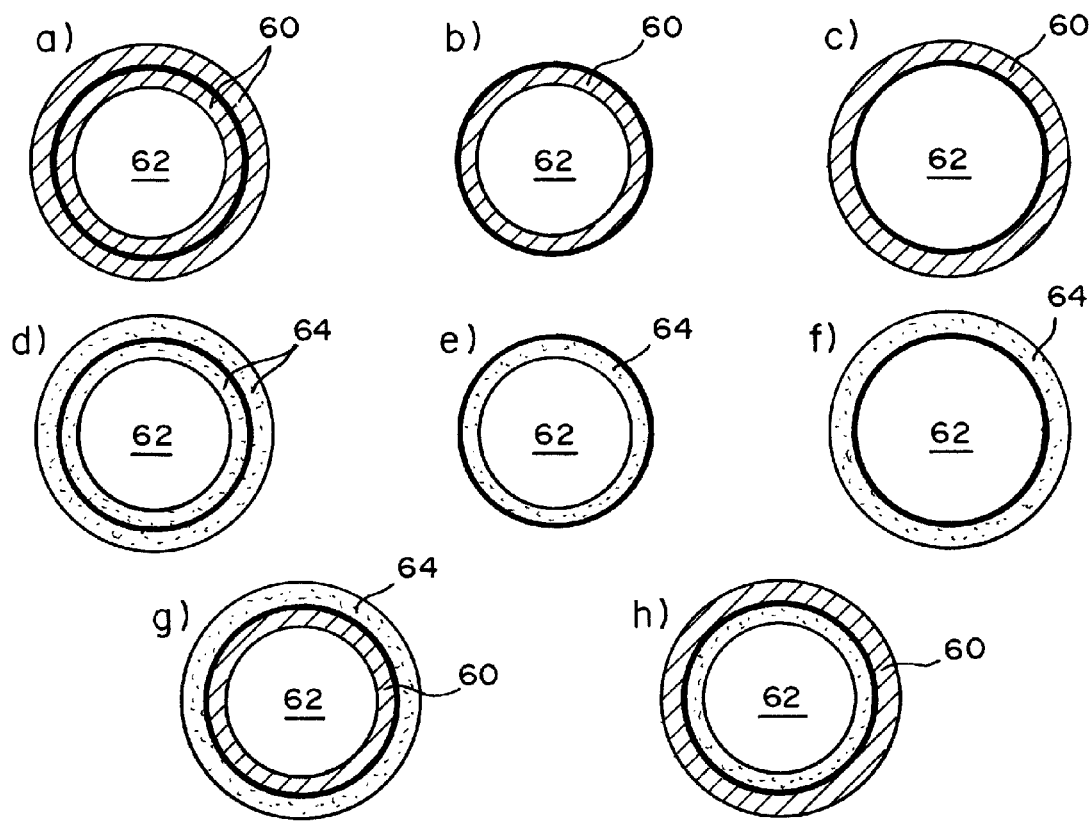
FIG. 5B is a schematic representation of possible stent coating combinations, exemplifying the surface specific coating of protoelastin or other agents. Plasma polymerised stent is represented in black in each case. Protoelastin coating is represented in grey and 'other' coating in dashed line (anti-restenosis agent for example). Schematic shows protoelastin coating (a) both sides, b) the luminal side only and c) the mural (ablumnial) side only. Also shown is 'other' coatings on (d) both sides, e) the luminal side only and f) the mural (ablumnial) side only. A stent with a luminal protoelastin coating and mural (abluminal) 'other' coating is shown in g)—with the reverse of this shown in h).

FIG. 5A demonstrates coating permutations for selectively plasma polymerised tropoelastin 60 coated polymerization on a stent 62. The plasma polymerisation treatment can be on either the luminal or mural side, or both. FIG. 5B shows coating permutations once the stents 62 are plasma polymerised. It may be advantageous to coat only one side with protoelastin 60, though both sides can be treated. Drugs can be incorporated in combination with protoelastin 64 and another coating. Each of these could be on the luminal and/or mural surface.

The protein can also be used to form coatings on materials such as microchips, which may be formed of a material such as a silicon chip, which may be used as sensors, electrodes, or for drug delivery, or a device such as an implantable pump.

2. Implants and Prosthetics

Other useful materials are matrices for tissue engineering and/or drug delivery, bone implants and prosthetics including pins, rivets, screws and rods, as well as artificial knees and other joints, especially at the surfaces where the metal, ceramic or bone interfaces with the host tissue. In the majority of these cases, the critical role of the protoelastin is to increase the biocompatibility of the implant or matrix, promoting cell attachment or diminishing the formation of scar tissue, abnormal proliferation of cells (i.e., restenosis or scarring), and integration of the implant into the host.

1. Crosslinking of Elastin

The protoelastin can be an enzymatically or chemically cross-linked to itself, to one or more other polymers or to a substrate. Enzymatic cross-linking can be achieved using any lysyl oxidase capable of converting epsilon amines to adipic semi-aldehydes or through the enzyme catalysis of transglutaminase. The chemical cross-linking can be achieved using any from the group of reagents with at least one amine reactive group, for example, using a chemical cross-linking reagent such as bis(sulfosuccinimidyl)suberate (BS3), 1-Ethyl-3-[3-dimethylaminopropyl]carbodiimide Hydrochloride) (EDC), glutaraldehyde, N-hydroxysuccinimide) (NHS) and 1,6-diisocyanatohexane (HMDI) and combinations thereof.

2. Methods of Making Coatings and Covalent Coupling to a Substrate

The tropoelastin can be applied to a surface by spraying, dipping, or other methods known to those skilled in the art.

In one embodiment the substrate material is modified to create reactive surface groups which facilitate covalent interaction. In the case of inert polymeric materials like ePTFE, the surface requires activation, Both 'classical' plasma processes (Bilek et al. (2004) In *Smart Materials III*, Vol. 5648 (Ed, Wilson, A. R.) SPIE, pp. 62-67) and higher energy plasma immersion ion implantation (Bilek, et al. *Surface and Coatings Technology*, 156:136-142 (2002)) (PIII) are applicable. In a preferred embodiment, the tropoelastin is covalently tethered to the polymer when a solution of the protein is incubated with the activated surface. PIII has recently been shown to increase the functional lifetime of attached proteins and may be preferred (Nosworthy, et al. *Acta Biomater*, 3:695-704 (2007)).

Figure 6:
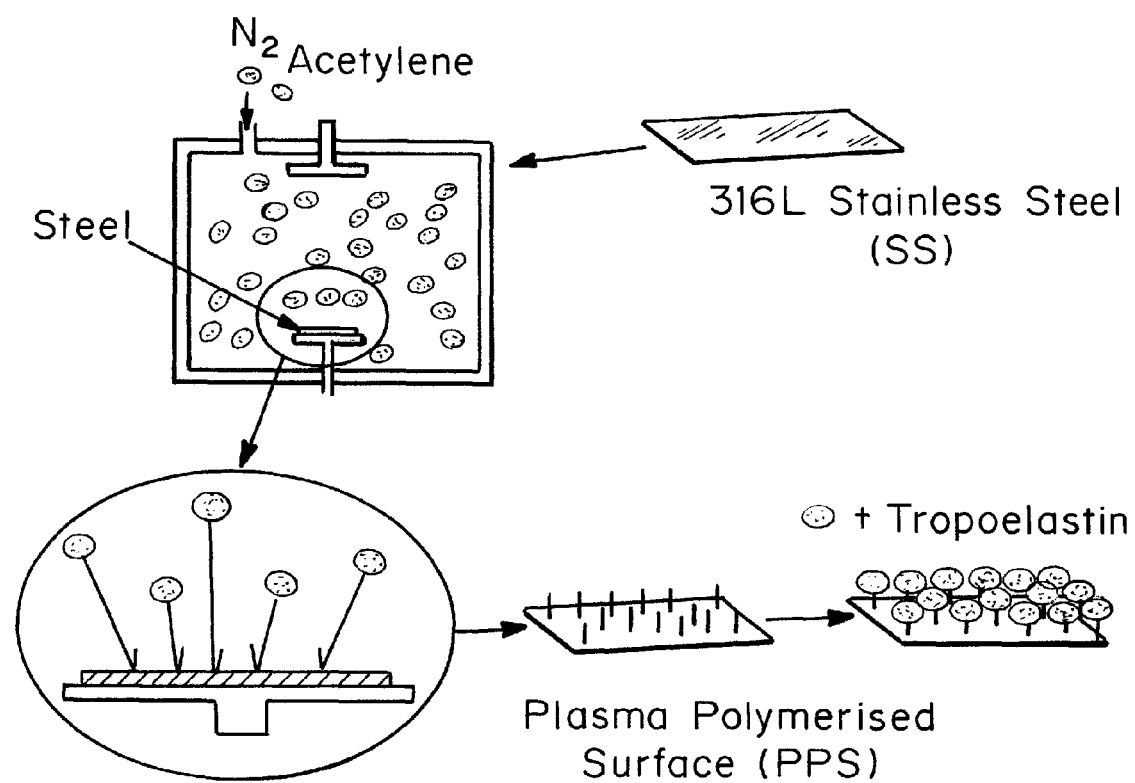
FIG. 6 is a schematic of the process of applying a coating to stent surface.

Metallic substrates can be also be functionalized by applying a modified plasma process to the substrate while it is immersed in a carbon containing plasma or in a vapour of the monomer used to deposit the plasma polymer layer or by codeposition of a graded substrate/polymer layer which terminates in the polymer (Yin, et al., *Surf. Coat. Technol.*, 203:1310-1316 (2009)). This is shown schematically in FIG. 6. A range of short chain carbon-based polymers including hexane and acetylene can be used to form the basis of the plasma polymer layer. The plasma chamber also contains a background carrier gas, examples of which include oxygen, hydrogen, argon, nitrogen and combinations thereof.

In a preferred embodiment acetylene is injected into the plasma chamber and activated together with a combination of nitrogen and argon background gas, subsequently condensing to form polymerized surfaces. This technique can be used to bind tropoelastin to a range of metals including stainless steel, as demonstrated by Yin, et al., *Biomaterials*, 30:1675-1681 (2009).

3. Methods of Making Laminates

The protoelastin can be in the form of a laminate, wherein the tropoelastin is layered onto one or more layers of polymer, preferably stabilized by cross-linking and/or covalent tethering to the substrate, which may then be covered with one or more additional layers of polymer. For vascular applications and implants that interface with cells or tissue, the luminal side of the laminate or exterior portion of the implant is preferable covered with the protoelastin. The selection of the polymer(s), the number and thickness of the polymer and tropoelastin layers, and the degree of cross-linking of the tropoelastin will determine the strength and rigidity of the laminate.

4. Methods of Making Polymer Blends

The tropoelastin can be blended with one or more polymers, as described above, to create materials having desired mechanical properties. The properties will depend on the polymer that is selected, the relative concentration of polymer to tropoelastin, and the method of blending and cross-linking or covalent coupling, if any.

The polymeric materials can be blended with the tropoelastin dissolved in an appropriate mutual solvent. For electrospinning, materials are best dissolved in polar organic solvents. 1,1,1,3,3,3-hexafluoropropanol (HFP) is preferred. Other solvents such as tetrahydrofuran (THF), N,N-dimethylformamide (DMF), trifluoroacetic acid (TFA) and dichloromethane can also be used. Tropoelastin blends can also be prepared in aqueous systems like phosphate buffered saline (PBS) for other fabrication techniques by taking advantage of its unique temperature behaviors (e.g. increased solubility at 4° C.).

5. Electrospinning of Fibers

Electrospinning of fine fibers provides the greatest control over the architecture of the constructs. By way of example, electrospun recombinant human tropoelastin has a tensile strength of about 0.5 MPa, but when it is co-spun with collagen in a 50:50 ratio, strength is doubled. When tropoelastin is electrospun with a polymer such as polycaprolactone, the strength of the final material is even greater (up to 3 MPa), while the elasticity contribution of elastin can be retained. Biostable polymers such as nylon and Dacron® are preferred.

Composite tubular materials that have favorable characteristics for grafting have been engineered using the electrospinning technique. The tubes are saturable, porous (when viewed by scanning electron microscopy) and can be reproducibly manufactured. In a preferred embodiment, the tubes are composites of tropoelastin and polycaprolactone, subsequently cross-linked with HMDI. Non-degradable or less degradable polymers that are used with the tropoelastin will be more stable.

The material can be applied as a part of a variety of clinical vascular applications including a vascular conduit, a stent, a stent-graft, a surgically or percutaneously implantable heart valve, a vascular/septal occlusion device, a vascular closure device or as a surface coating for a vascular device/application.

EXAMPLES

The present invention will be further understood by reference to the following non-limiting examples.

The examples describe the formation and characterisation of acetylene plasma polymerised stainless steel surfaces wherein the hydrophilic deposited interface is strongly attached to the metal substrate and resistant to supraphysiological physical forces. Covalent attachment of tropoelastin, an important blood contacting vascular protein, was determined to be in a porous monolayer, resulting in improved endothelial cell interactions. This technology provides the capacity to bind proteins to metallic surfaces and to retain protein function, thereby facilitating biological modulation of host responses to metallic prostheses, with particular relevance to endovascular implants such as stents.

The problem of appropriate biocompatibility extends to all metallic vascular devices including heart valves, pacemakers and stents. These devices interact poorly with host cells and tissue, inducing inflammation at the site of implantation and increasing the long term risk of thrombosis. In the case of metal valves, this means that patients have to remain on long term anticoagulation, with their attendant bleeding risks. For endovascular applications, incomplete re-endothelialisation is a key concern, given that an intact endothelium is critical to both modulating vascular tone and deterring thrombus formation. Recent data has shown that coronary stents are prone to both acute and late thrombotic events, with clinically catastrophic consequences. In particular, drug-eluting stents, by inhibiting local cell proliferation, dramatically impair endothelialisation at the site of stent deployment, thereby leaving the patient at long term risk of thrombosis. This risk of stent thromboses is a critical unresolved problem in cardiovascular medicine.

To be applicable to vascular biomaterials applications, the plasma polymerised surface needs to be physically robust. Tensile testing of the plasma deposited coating and substrate interface found that the bonding between the layers was very strong. The ultimate tensile strength was found to be similar to that of some common polymers, such as polyethylene, and in excess of the requirements for a coating. To verify this assertion, plasma polymerised surfaces were subjected to pulsed shear flow, simulating conditions that would be relevant for use as a vascular biomaterial coating. Under forces ten times greater than those found in vivo no reduction in the coating thickness was observed after three weeks. Taken together, these results showed that the deposited surface was resilient to supraphysiological physical forces.

Equally important in the design of an improved vascular biomaterial is the functional presentation and full uniform coverage of the immobilised protein layer. Commercially available heparin-immobilised ePTFE emphasizes the clinical importance of these features. The improved performance of these grafts over untreated ePTFE is attributed to both the uniformity and bioactive presentation of the heparin coating, which is covalently tethered to the graft material.

The examples demonstrate that plasma coated surfaces were significantly better at binding protein layers and maintaining their biological activity than untreated stainless steel. Comparing three different polymerisation carrier gas conditions, bioactivity at day 10 was best retained using both nitrogen and argon in the acetylene polymerising gas. The $N_2$/Ar samples were therefore used for tropoelastin attachment and subsequent analysis using QCM-D and spectroscopic ellipsometry.

Having developed a coating platform technology that may improve the compatibility of vascular prosthesis by protein binding, tropoelastin was tested as a candidate to enhance biomimicry. Its use recognises the importance of tropoelastin, and corresponding biopolymer elastin to both the physical and biological properties of vasculature. Elastin is a critical cell regulatory protein in the vascular wall, while elastin-based sequences reduced acute thrombogenicity when used as coatings in a baboon shunt model. The interaction of tropoelastin with the plasma deposited surfaces was investigated using an ELISA assay. The absorbance above background in the ELISA is indicative of the surface concentration of exposed tropoelastin binding motifs recognised by the antibody. After coating and rinsing in PBS, the amount of protein bound to control stainless steel and plasma polymerised stainless steel was comparable. However, after SDS washing the difference was considerable: the majority of the protein was washed off the control surface whilst remaining virtually unchanged on the treated substrate. The fact that the SDS cannot remove the surface layer of tropoelastin indicates that this layer is covalently attached. The tropoelastin attachment dynamics were further tested using a quartz crystal microbalance. The QCM-D result indicated that the first layer of tropoelastin attached is covalently bonded, in agreement with the ELISA findings, while subsequent layers of the protein are physisorbed. The physisorbed layers can be washed away in buffer or SDS detergent, while underneath a monolayer is retained. The covalently bound layer was more thoroughly examined using ellipsometry. The low refractive index obtained after the 1 h incubation time indicates that the layer is not a complete monolayer, but more porous.

The initial functional aim was to improve the endothelialisation of the surface, recognising the importance of this aspect of vascular biomaterial design. The attachment and proliferation of human umbilical vein endothelial cells as a marker of endothelial cell affinity was measured. It was found that tropoelastin immobilised plasma polymerised surface had significantly greater short term HUVEC attachment and proliferation as compared to control stainless steel. Tropoelastin and sequence derivatives have been shown to support endothelial cell recruitment and growth and to play a significant role in migration and angiogenesis. However, this is the first demonstration that this bioactivity could be maintained with the protein immobilised covalently on a metal substrate, suitable for device applications.

In summary, the results demonstrate that plasma polymerisation of acetylene on metallic materials provides a robust interface, suitable for the immobilisation of biomolecules. Tropoelastin, which was covalently bound in a porous monolayer, encouraged the attachment of endothelial cells and enhanced their proliferation. This technology has broad applicability to a range of vascular applications as it is suitable for use on most materials. It allows for the modulation of the biological properties of blood contacting metal implants and could lead to improved biocompatibility.

Example 1

Protoelastin Synthesis Using Chemical Cross-Linking of Tropoelastin

Tropoelastin was dissolved in cold phosphate buffered saline (PBS) at a concentration of 100 mg/ml. The amine reactive cross-linker, bis(sulfosuccinimidyl)suberate (BS3) was freshly prepared by dissolving in PBS immediately prior to use to a concentration of 100 mM. The solutions were mixed in a 1:10 ratio to give a final cross-linker concentration of 10 mM. The solution was poured into a mould, prior to placement at 37° C. to facilitate coacervation and cross-linking. The resulting protoelastin was washed repeatedly with PBS and stored in a sterile environment.

Example 2

Protoelastin Synthesis Using HMDI 100 mg of tropoelastin was placed in a small weigh boat. In 10 aliquots, 100 µl of PBS was added to the tropoelastin slowly over several minutes. With the addition of each aliquot, a spatula was used to fold the solution into the protein. The tropoelastin eventually took on a gum-like consistency, which could be drawn to fibers and molded into shapes. To fix, the protein was submerged in a 10% 1,6-diisocyanatohexane (HMDI) in propanol solution and allowed to stand overnight. Elasticity was restored to the protoelastin by repeated washing in water and then in PBS.

Example 3

Protoelastin Materials Prepared by Electrospinning

The electrospinning method was adapted from (Li et al., 2005). Briefly, a tropoelastin solution (5% w/v) was mixed with a copolymer (5% w/v) in 1,1,1,3,3,3-hexafluoropropanol. The homogenous solution was loaded into a 1 ml plastic syringe equipped with a blunt 18 gauge needle. Constant flow rates (0.5 ml/h) were achieved using a syringe pump (SP100 IZ Syringe Pump, Protech International) and the needle connected to the positive output of a high voltage power supply (ES30P/20W, Gamma High Voltage Research Inc.). The metallic target for the fibers carried a negative charge, provided by a second power supply. Electrospinning was carried out with the needle voltage set at 20 kV, the target voltage set at −3 kV and with an air gap distance of approximately 15 cm. Electrospun fibers were cross-linked using a 10% HMDI solution in isopropanol and washed with water and PBS.

Example 4

Plasma Deposition or Protoelastin

Materials and Methods
Expression of Tropoelastin
Recombinant human tropoelastin corresponding to amino acid residues 27-724 of GenBank entry AAC98394 (gi 182020) was expressed and purified as previously described (Wu, et A, *J. Biol. Chem.*, 274(31):21719-24 (1999)). 316L stainless steel foil was purchased from Brown Metal, USA, and plasma cleaned before use. Horseradish peroxidase (HRP), tetramethylbenzidine (TMB), [2,2'-azino-bis(3-ethylbenzthiazoline-6-sulphonic acid)] (ARTS), anti-elastin (mouse IgG1) clone BA-4 antibody, anti-mouse IgG HRP and 4',6-diamidino-2-phenylindole (DAN) were all purchased from Sigma. All other reagents were of analytical grade.

Plasma Deposition of Tropoelastin on Steel Surface
The covalent attachment of tropoelastin to a metallic substrate has not been previously achieved and required the development of a unique metal/protein interface. The physical characteristics of the new plasma polymerised surface were extensively characterized, measuring the roughness, hydrophobicity and adhesion strength of the surface coating. Following this, the interface was optimised to retain the bioactivity of the immobilised species, at first using HRP as a model system. To the optimised surface tropoelastin was bound and its binding density and mechanics studied before the response of endothelial cells to the protein covered surface was assessed.

The preferred plasma deposition method was adapted from plasma enhanced chemical vapour deposition (Collins and Ferlauto, *Curr. Opin. Solid State Mater. Sci.*, 6:425-437 (2002) and U.S. Pat. No. 5,304,398). The system includes two plasma producing electrodes: the first is a radio frequency (RF) capacitively coupled electrode while the second is a pulsed direct current (DC) voltage source. The RF electrode is powered using an ENI-6B RF generator through an ENI-Matchwork matching network. The pulsed DC electrode was driven using an RUP-3 pulse generator from GBS-Elektronik (Germany). Surfaces to be coated were placed on the DC pulsed electrode, which was immersed into the plasma generated by the RF electrode. Acetylene was injected into the plasma chamber to react and form a polymer-like coating on the exposed surfaces. Nitrogen and argon at various flow rates were also deployed in the gas mix. The gas flow rates were regulated by MKS mass flow controllers. All experiments were conducted without heating or cooling of substrates, Surface Roughness and Contact Angle Measurements The plasma coated steel surface was characterised for roughness using atomic force microscopy (AFM, Autoprobe CP). Surface contact angle measurements were performed at 23±1° C. using a DSA10-MK2 contact angle analyser. Sessile water and formamide drops of 5 µl were used for advancing contact angle analysis using the method described by the manufacturer.

Adhesion Strength

An Instron 5567 adhesion tensile tester was used to determine adhesion strength of the plasma deposited coatings. For the adhesion strength analysis, the backside of the sample was glued onto a 10 mm diameter disc and the front surface was glued onto a 5 mm diameter disc. The strength of the coating adhesion was determined by applying tensile stress until fracture occurred.

Wear Due to Shear Flow

A liquid pulse flow inducer (Watson Marlow) was used to produce a pulsed shear force on the coated surfaces to simulate flow conditions in human arteries. The coated surfaces were placed into a 5 mm diameter tube in the pulsed flow circuit for testing and glycerol mixed with de-ionised water was used as the shearing fluid. The wear caused by the pulsed flow was studied using microscopy and spectroscopic ellipsometry, Assessment of Bioactivity Retention The bioactivity of surface attached HRP was assessed using a colorimetric assay as described recently in detail (Steel, et al., *Biophys. Jour.*, 91(6):L66-8 (2006)). HRP provides a robust model of surface bound activity and produces an easily identifiable coloured by-product. HRP was buffered in a solution of 10 mM $PO_4$ at pH 7.0 and surface attachment was achieved by incubating overnight in HRP at 50 µg/ml. Four cycles of washes for 20 min on each substrate were then carried out. After the first, the washing container was changed so the next three washes were in a fresh clean container. The surface was tested for the presence of functional HRP by covering with TMB solution. After exposing to TMB the colour was allowed to develop for 30 secs. The reaction was stopped with hydrochloric acid and the colour was read using a spectrophotometer at 450 nm.

Detection of Bound Tropoelastin and Assessment of Strength of Attachment Using SDS Washing An enzyme-linked immunosorbant assay (ELISA), with an anti-elastin primary antibody was employed to detect the presence of tropoelastin on plasma polymerised surfaces, before and after SDS washing. Uncoated and coated 316L stainless steel foil samples were cut into 0.8×L2 cm rectangles and placed into the wells of a 24-well plate. Tropoelastin was incubated with samples at 4° C. for 16 h. Unbound tropoelastin was removed by aspiration and the samples were washed with PBS. The samples were transferred to 5% SDS (w/v) in PBS and incubated at 90° C. for 10 min. Non SDS-treated samples were washed in PBS alone. The samples were returned to the 24-well plate and washed again. Non-specific binding was blocked with 3% (w/v) bovine serum albumin (BSA) in PBS for 1 h at room temperature. Following BSA blocking the samples were incubated sequentially with mouse anti-elastin antibody (BA-4) and goat anti-mouse IgG-HRP conjugated secondary antibody for 1 h at room temperature. After every step the samples were washed three times with PBS. The samples were transferred to a new 24-well plate and ABTS solution (40 mM ABTS in 0.1 M NaOAc, 0.05 M $NaH_2PO_4$, pH 5, containing 0.01% (v/v) $H_2O_2$) was added and incubated at 37° C. After 30-40 min the plates were agitated and 100 µl aliquots of the ABTS were transferred to a 96-well plate and the absorbance was read at 405 inn using a plate reader.

Quartz Crystal Mircobalance Quantification of Tropoelastin Attachment

A QCM-D Q-sense E4 quartz crystal microbalance was used to characterise the attachment and de-attachment of tropoelastin. The plasma coated surfaces were placed onto a 5 MHz quartz crystal oscillator with gold electrode. The diameter of the quartz crystal was 13 mm with an effective sensing area of diameter 5 mm. All QCM-D analysis was performed at 25° C. and solution was pumped over the quartz crystal surface at a flow rate of 150 ml/min.

Ellipsometric Analysis of the Immobilisation of Tropoelastin onto Plasma Polymer Surfaces Spectroscopic ellipsometry was used to give complementary information about tropoelastin attachment and coverage. The characterisation was conducted using a J. A. Woollam M-2000 spectroscopic ellipsometer for the visible wavelength range. Silicon wafers were used in place of stainless steel so as to provide a highly smooth interface with the plasma polymer coatings. Samples taken from PBS solution were rinsed in de-ionised water 5 times and dried in mild nitrogen gas flow prior to being placed in the spectroscopic ellipsometer for measurement. Data was collected on the plasma coated silicon wafers at three angles of incidence (65°, 70°, and 75°) before plasma coating, after plasma coating, and then again after tropoelastin attachment. A model was fitted for each data set with the unknown parameters restricted to the top most layer. The parameters used for the previous layers were imported from models fitted to the preceding data sets.

Results

Covalent Attachment of Tropoelastin to Polymerized Stainless Steel

Figure 7:
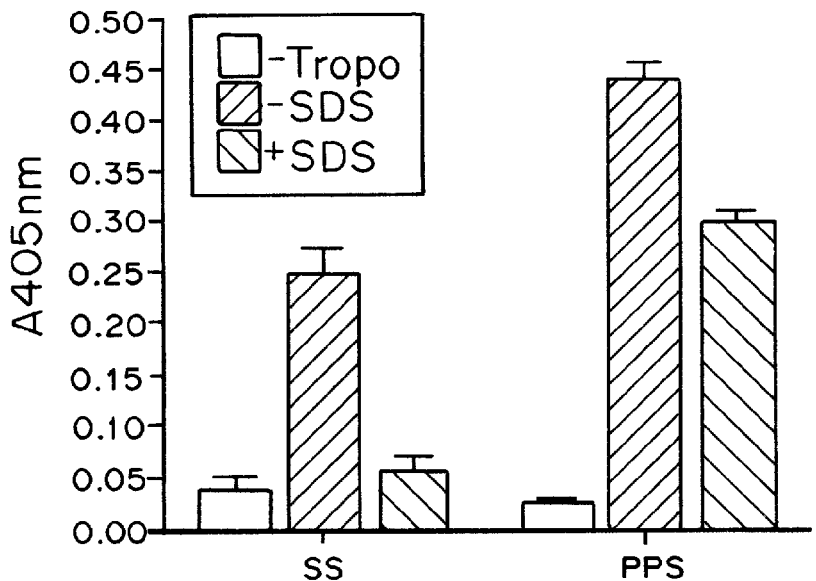
FIG. 7 is a graph of an anti-elastin ELISA, used to detect tropoelastin bound to PPS treated steel surfaces, compared with control steel, which shows that covalent (SDS resistant) bonds are formed with the protein on the PPS.

FIG. 7 is a graph of detergent washing of bound protoelastin from stainless steel surfaces (SS, stainless steel only; PPS, stainless steel with plasma polymerised coating). No protoelastin is shown in the controls on the left for the stainless steel, with protein but no washing in middle, and with protein and sodium dodecyl sulfates (SDS) washing on right. SDS was used to try to remove protoelastin coated onto either untreated stainless steel or plasma polymerized stainless steel. A significant reduction in protoelastin was observed for the untreated case, while considerably more protein remained attached to the treated surface.

Surface Roughness and Contact Angle Measurements

Surface roughness of the acetylene plasma coating deposited on a polished silicon substrate surface was characterised using AFM. The coated surfaces were found to be very smooth. The typical tins roughness was 1-2 nm (c.f. substrate RMS roughness of about 0.5 nm).

The contact angles of water and formamide were measured as a function of time. The water contact angles increased slightly in the first two days before stabilising. After 2 days, the water contact angle measured on the plasma coated surfaces was 62±7°, indicating that the surfaces are hydrophilic. In comparison, most polymeric surfaces are hydrophobic having contact angles of over 90°.

Adhesion Strength

The adhesion strength of the deposited layer as measured by the tensile test method, using a contact area of 5 mm diameter and straining to failure at the coating interface, was typically more than 15 MPa for coatings deposited on stainless steel foils. This value is comparable to or larger than the ultimate tensile strength of polyethylene and is indicative of a well adhered coating.

Wear Due to Shear Flow

The wear resistance of the plasma coated surfaces against shear forces induced by fluid flow was determined to be high using a pulsed flow inducer. The liquid pulse flow inducer produced a pulsed shear force on the coated surfaces to simulate the mechanical impact in human blood vessels using a flow of 60% glycerol mixed with de-ionised water at a temperature of 10° C. The pulse flow rate was 500 ml/min with 100 pulses/min so as to accelerate the wear test, resulting in a shear force on the surfaces equivalent to approximately 10 times the shear force in human arterial blood vessels. No thickness reduction was detected for coatings deposited on polished silicon substrates after 3 weeks continuous flow stressing using spectroscopic ellipsometry.

Example 5

Blood Compatibility Testing

A. Thrombogenicity Testing Using APTT Assay

Materials and Methods

The thrombogenicity of protoelastin was assessed in vitro, using an activated partial thromboplastin time (APTT) assay (Cullberg et al., Br. J. Clin. Pharmacol., 51(1):71-9 (2001). This assay determines the ability of a material to effect the activation of the contact factors of coagulation and thus change the clotting time of human plasma.

Normal citrated plasma was mixed with a kaolin-phospholipid suspension (5 g/l in PBS) and left at 37° C. for 10 min, with occasional shaking. At exactly 10 min, pre-warmed CaCl$_2$ (0.025M) was added and a stopwatch started. The time for the mixture to clot was recorded. The protocol was repeated for plasma containing saline or ground protoelastin particles instead of kaolin, and again clotting times were recorded.

Results

Figure 8:
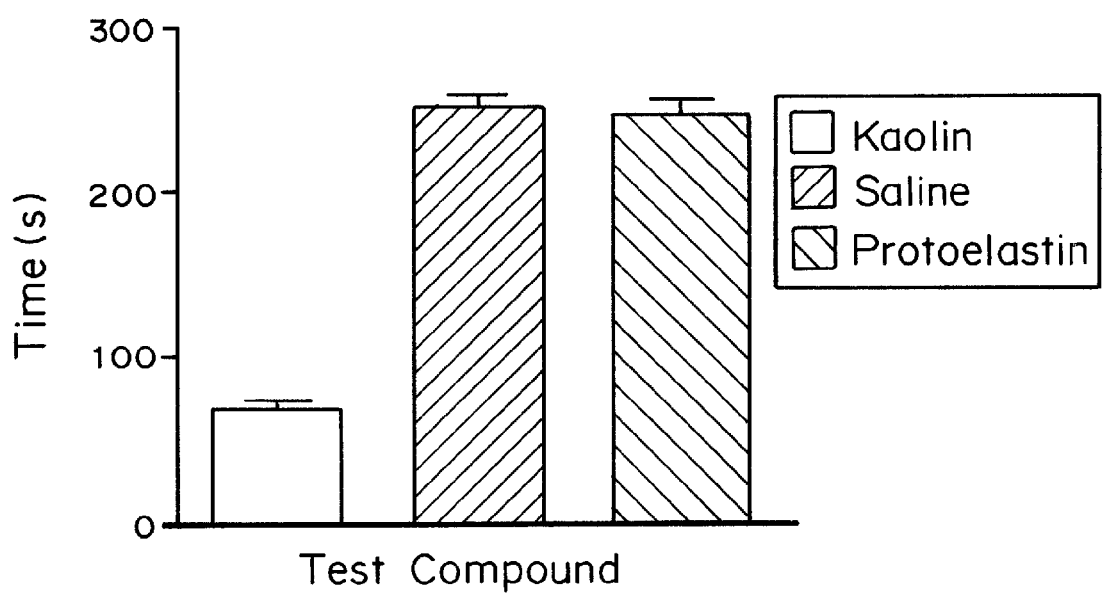
FIG. 8 is a graph of the clotting time (in seconds) for human plasma treated with kaolin (positive control), saline (negative control), and protoelastin, showing the clotting times for the saline and protoelastin are not significantly different.

Results are shown in FIG. 8 and demonstrate the non-thrombogenicity of the elastin coated material. The clotting time is indicated in seconds; the test compound on the left was kaolin; middle was control saline; right was protoelastin. There was no difference between saline and protoelastin.

B. Platelet Aggregation Testing Using Radiolabelled Platelet Assay

Materials and Methods

Platelets were isolated from blood and labelled with Indium-111 oxine. Labelled platelets were resuspended in heparanised blood and injected onto stainless steel samples: either steel alone, plasma polymerised steel, or plasma polymerised coated with protoelastin. Samples were rocked for 45 mins at 37° C. before washing with PBS and gamma counting (Cao, et al., J. Biomed. Mater. Res. Part A, 79(4):788-803 (2006)).

C. Static Plate Thrombogenicity Assay

Materials and Methods

Heparinised whole blood (0.5 U/ml) was added to steel samples (1.2×0.9 cm) in a 24-well plate. Control SS was compared to PPS alone, PPS coated with tropoelastin (20 µg/ml) and PPS coated with heparin (5 U/ml). Coatings were left overnight at 4° C., prior to the experiment to covalently attach. Each well received 1 ml of blood before incubation at room temperature for 1 hour, while rocking. Samples were washed 3 times with PBS and photographed.

Results

Comparison of stainless steel samples (control and treated) exposed to blood in a static clotting assay shows that PPS treatment, as well as tropoelastin or heparin coating, reduces thrombus formation. The amount of clot present is negligible in all of the treatment cases, in contrast to the large amount seen on the untreated stainless steel. In this assay plasma polymerised stainless steel alone seems to perform as well as tropoelastin or heparin coated variants.

D. Thrombogenicity Testing Using Chandler Loop Assay

Materials and Methods

An in vitro clotting assay was developed, modified from Chandler A. B. 1958 Laboratory Investigation; 7: (2) 110-114. Tygon S-50-HL tubing (Professional Plastics USA, internal diameter 0.250", outer diameter 0.312") was cut to 28 cm in length. A piece of stainless steel (1.2×0.5 cm) was inserted approximately 3 cm into one end of the tubing and made flush against the inner wall of the tubing by inflation of a 6 mm balloon catheter. The tubing was connected into a loop with a 1 cm long silicon connector. The loop was filled with 2.5 ml of heparinized blood via two 21 gauge needles inserted under the silicon connector, one as the inlet port and one as the outlet port. The Heparin used was 0.5 U/ml, from porcine intestinal mucosa, Sigma). Three loops were made for each sample: stainless steel (SS), plasma polymerised steel (PPS) coated with tropoelastin and PPS coated with 5 U/ml Heparin. The loops were placed on a tilted rotating wheel and rotated at 34 rpm at 37° C., with observation every 15 minutes until a thrombi had formed in the SS loops.

The blood, thrombus and steel were removed from the loop, washed twice in PBS, blotted dry and photographed. The steel and thrombus was weighed. After this the steel was placed in 500 µl distilled water and left overnight. The absorbance was measured at 570 nm.

To the blood from each loop (approximately 2 ml), 200 µl acid citrate dextrose (ACD, Sigma) was added and these were centrifuged at 1000 rpm for 15 minutes to obtain the serum. This was used to detect the level of soluble p-Selectin by ELISA using a kit from R&D Systems (USA).

Results

Figure 9A:
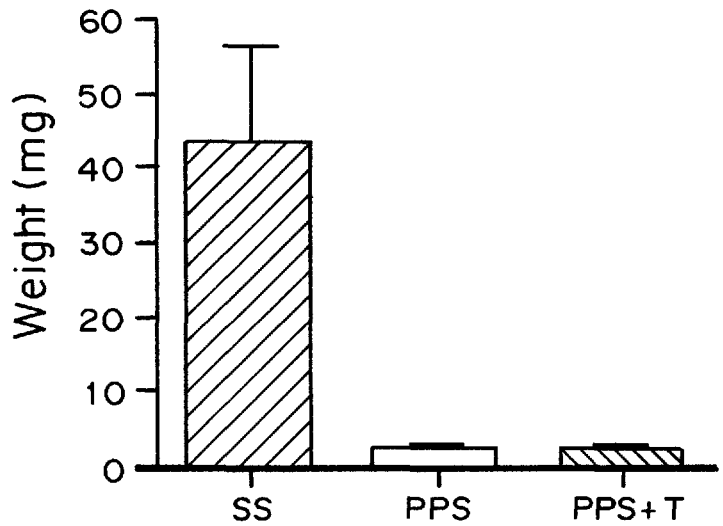
FIG. 9A is a graph showing the amount of thrombus (mg) formed after Chandler Loop exposure for 30 mins. Graph compares stainless steel (SS), to plasma polymerised steel (PPS) and plasma polymerised steel+tropoelastin (PPS+T).
Figure 9B:
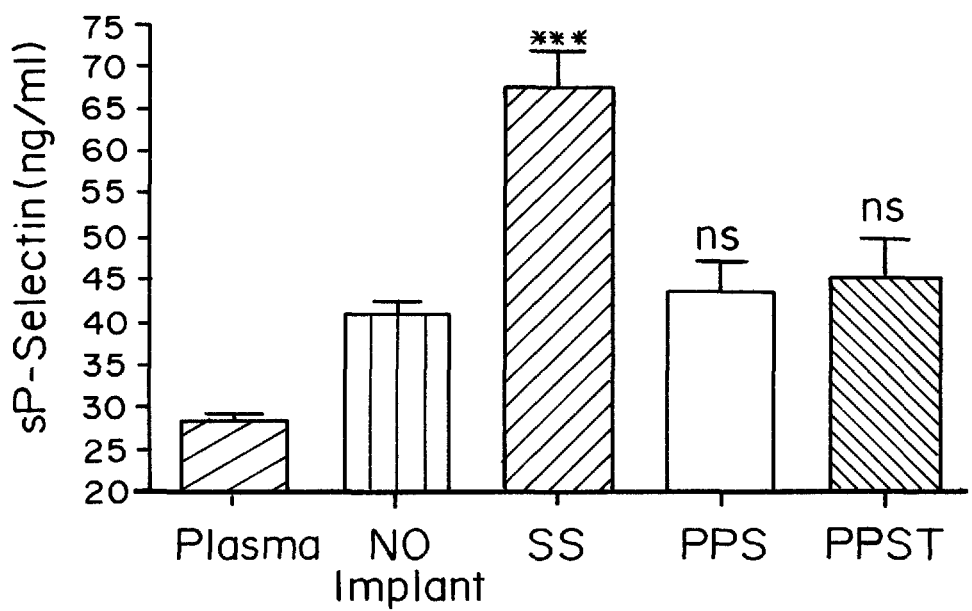
FIG. 9B is a graph of soluble P-selectin (ng/ml) measured by ELISA showing that the amount of p-selectin is reduced on tropoelastin coated PPS. 'Plasma' represents the basal level of sP-selectin prior to contact with the Chandler Loop.

A clear difference in the amount of clotting was seen between the samples taken from the loops. Comparison of stainless steel samples (control and treated) exposed to blood in a modified chandler loop assay shows that PPS with a tropoelastin or heparin coating reduces thrombus formation. FIG. 9A shows the relative amount of thrombus weight for these samples. FIG. 9B is a soluble P-selectin ELISA showing the amount of p-selectin is reduced on tropoelastin coated PPS.

The amount present was clearly lower in both of the treatment cases, in agreement with the observations from the static clotting system. This observation was quantified by weighing the thrombus generated by each material in the loop. Both PSS alone and PPS coated with tropoelastin confer a significant benefit compared to stainless steel alone, though these are not significantly different from each other. (FIG. 9A, using a one-way ANOVA, ***p<0.001.)

In addition to the absorbance measurement, the amount of p-selectin present in the exposed blood was quantified using an ELISA. The presence of stainless steel in the Chandler loop significantly increased p-selectin levels as control blood circulated in the loop with no implant present. Plasma polymerised stainless steel coated alone, and coated with tropoelastin, were not significantly different from the no implant control (FIG. 9B, using a one-way ANOVA, ***p<0.01). The plasma sample is the negative control in this case, showing the basal level of p-selection in the blood prior to exposure to the Chandler loop.

Example 6

Detection of Bound Tropoelastin and Assessment of Strength of Attachment Using SDS Washing Materials and Methods An ELISA with an anti-elastin primary antibody was employed to detect the presence of tropoelastin on plasma polymerised Surfaces, before and after SDS washing. Uncoated and coated 316L stainless steel foil samples were cut into 0.8×1.2 cm rectangles and placed into the wells of a 24-well plate. Tropoelastin was incubated with samples at 4° C. for 16 h. Unbound tropoelastin was removed by aspiration and the samples were washed with PBS. The samples were transferred to 5% SDS (w/v) in PBS and incubated at 90° C. for 10 min. Non SDS-treated samples were washed in PBS alone. The samples were returned to the 24-well plate and washed again. Non-specific binding was blocked with 3% (w/v) bovine serum albumin (BSA) in PBS for 1 h at room temperature. Following BSA blocking the samples were incubated sequentially with mouse anti-elastin antibody (BA-4) and goat anti-mouse IgG-HRP conjugated secondary antibody for 1 h at room temperature. After every step the samples were washed three times with PBS. The samples were transferred to a new 24-well plate and ABTS solution (40 mM ABTS in 0.1 M NaOAc, 0.05 M $NaH_2PO_4$, pH 5, containing 0.01% (v/v) $H_2O_2$) was added and incubated at 37° C. After 30-40 min the plates were agitated and 100 µl aliquots of the ABTS were transferred to a 96-well plate and the absorbance was read at 405 nm using a plate reader.

QCM-D was also used to study the dynamics of the attachment of tropoelastin to the plasma deposited surfaces. Spectroscopic ellipsometry was used to complement the QCM-D analysis by determining the thickness and optical constants of the attached tropoelastin layer.

Results

Tropoelastin was immobilised onto control and plasma polymerised stainless steel surfaces. Using an ELISA, tropoelastin attachment was measured on these surfaces before and after washing with SDS detergent. A control surface with no tropoelastin bound was included to demonstrate the background signal due to non-specific attachment of the antibody. The plasma polymerised stainless steel surface produced a significantly higher absorbance compared with the untreated stainless steel. SDS effectively removed the tropoelastin from the stainless steel surface but not from the plasma deposited surface, indicating superior covalent attachment to the latter.

The mass change during the surface attachment of tropoelastin and subsequent rinsing with SDS detergent was measured using QCM-D. As tropoelastin attaches to the surfaces coated onto oscillating quartz crystals, a shift in the resonant frequency and a change of dissipation factor (inversely proportional to quality factor Q) are observed. The shift in resonant frequency is proportional to the change in mass associated with a surface attached protein layer.

Initially, the plasma deposited surface was stabilised in 10 mM phosphate buffer (PB) at pH 7.0 for about 1 h. Then tropoelastin (concentration 500 □g/ml) in PB buffer was introduced into the flow cell containing the quartz crystal. A rapid mass increase associated with protein attachment to the surface was observed in the initial stage of the assay. The rate of attachment declined over time and after about 10 minutes of exposure the attached mass reached a maximum close to 800 ng/cm$^2$. Taking into account the molecular mass of the tropoelastin used here was 60 kDa and assuming the footprint of tropoelastin in its native state is 30 nm$^2$, the monolayer mass should be approximately 350 ng/cm$^2$.

Reverting to flow of fresh buffer resulted in a removal of some of the previously attached mass. Initiation of the flow of SDS detergent appears to give an immediate jump in the apparent mass absorbed. This is an artefact associated with differences in the viscous properties of the SDS and PB solutions and should not be interpreted as an instantaneous change in the adsorbed protein mass. The subsequent steep decrease of the curve however is associated with the removal of surface attached tropoelastin. Once the SDS flow is replaced with PB again, it can be seen that the mass of the attached protein layer has been reduced to about 220 ng/cm$^2$. An attempt to clean further with 90% ethanol in water did not change the tropoelastin attachment. Once again the temporary excursion during the ethanol solution flow is a result of its different viscous properties. The mass remaining after SDS and ethanol washing is less than the mass of a monolayer of tropoelastin, suggesting that the SDS resistant layer, which we assume to be covalently bonded to the plasma deposited surface, is porous.

Example 7

HUVEC Attachment and Proliferation and Thrombogenicity on Coated Surfaces

A. Attachment to Protoelastin

Materials and Method

The effect of fibronectin, tropoelastin, heparin and a combination of tropoelastin and heparin on human umbilical vein endothelial cell (HUVEC) attachment was assessed in comparison to BSA blocked (10 mgml) tissue culture plastic. Cultures were plated on 48-well culture plates and the cells cultured at 37° C. After 1 h, triplicate wells of cells were washed and fixed with 3.7% formaldehyde for 20 min. The formaldehyde was aspirated and the wells washed three times with 500 µl PBS. Attached cells were stained by adding 100 µl 0.1% (w/v) crystal violet solution to each well for 1 h at room temperature. The crystal violet was aspirated and the wells washed once with 500 µl distilled (d) $H_2O$, followed by three times with 400 µl d$H_2O$. The dye was solubilised by the addition of 200 µl of 10% (v/v) acetic acid per well and 100 µl transferred to a 96-well plate and absorbance measured at 570 nm.

Results

Figure 10A:
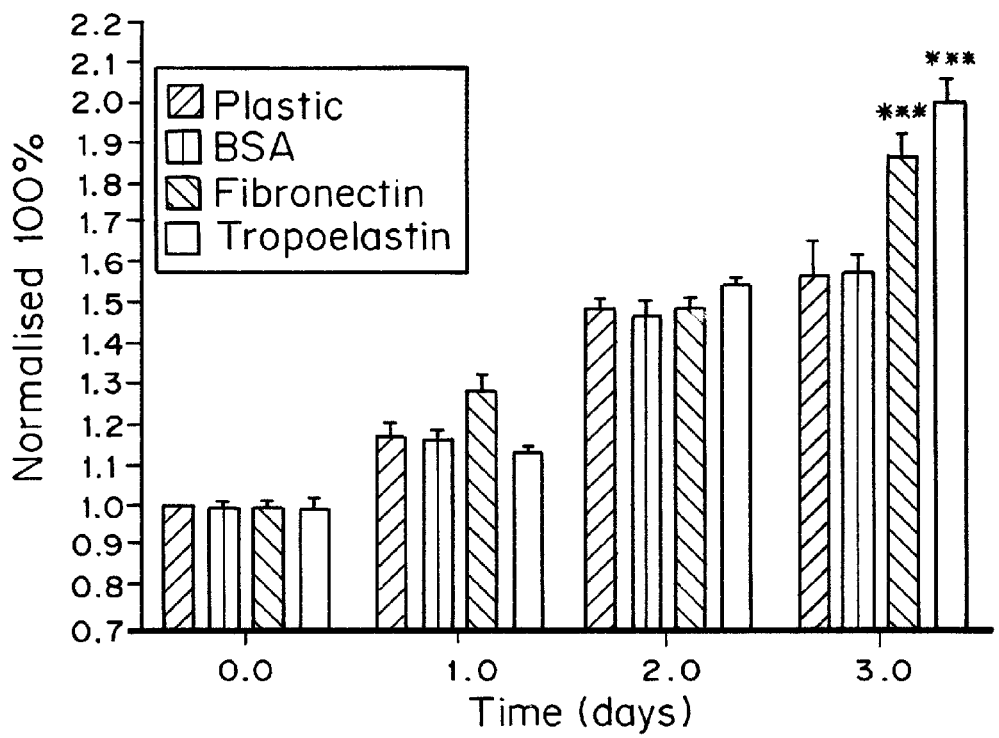
FIG. 10A is a graph of the growth of HUVECs (absorbance 490 nm) on tissue culture plastic that was uncoated, coated with bovine serum albumin, coated with fibronectin, or coated with protoelastin.

FIG. 10A demonstrates that cell attachment to tissue culture plastic blocked with heat-denatured BSA is negligible, making this condition the negative control. Cell attachment to fibronectin is considered to be total. HUVECs attached as well to tropoelastin as they do to fibronectin, but significantly worse to heparin coated wells. A coating consisting of a combination of tropoelastin and heparin partially rescues this.

B. Attachment to Tropoelastin Coated Steel

Materials and Methods

HUVECs were harvested enzymatically from male and female infant umbilical cords. Endothelial cells from passages 2-4 were used. HUVECs cultured for 48 h were lifted with 0.05% trypsin-EDTA and resuspended at 40,000 cells/mL. Cultures were plated on 48-well culture plates and the cells cultured at 37° C. After 1 h, triplicate wells of cells were washed and fixed with 3% formaldehyde for 20 min. Samples were treated with 0.2 M glycine for 20 min, 0.2% Triton® X-100 for 6 min, and blocked with 5% BSA for 1 h before staining cell nuclei with 0.15 µg/ml DAPI. Images from ten random fields were obtained with a fluorescent microscope and cell nuclei were counted using Image J. Attachment of cells to tropoelastin bound plasma polymerised stainless steel and plasma polymerised steel without tropoelastin was compared to untreated stainless steel controls.

Results

Figure 10B:
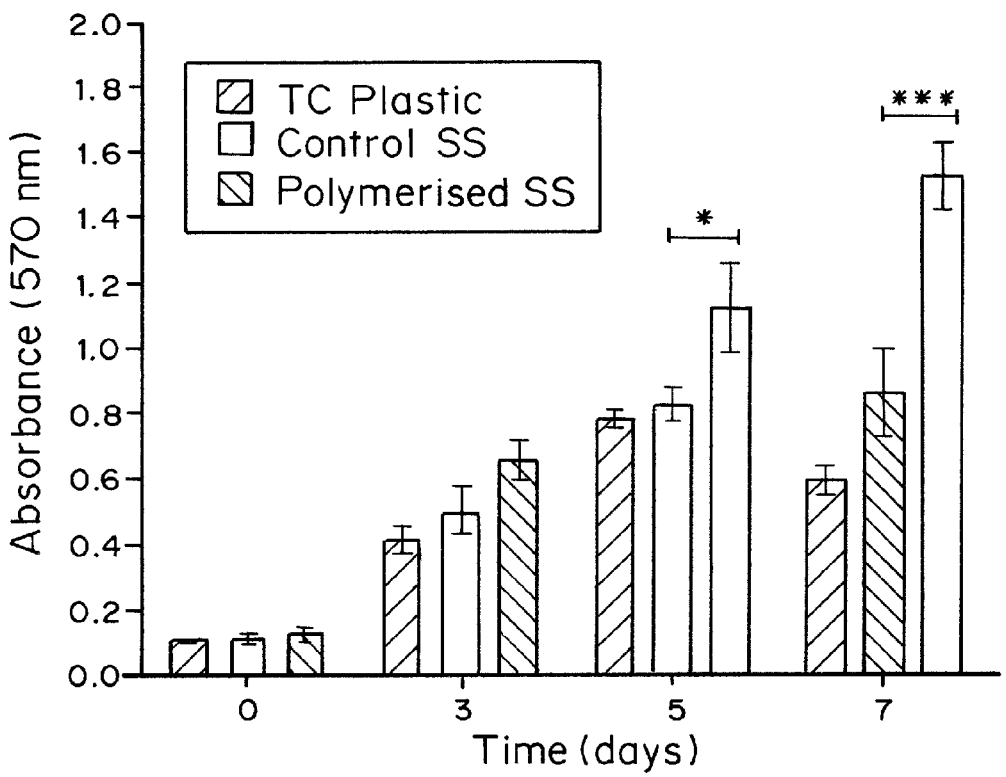
FIG. 10B is a graph of HUVEC proliferation on steel (control or treated), showing the superior growth of these cells on tropoelastin coated plasma polymerised surfaces.

Results are shown in FIG. 10B. The attachment of HUVECs to either control or plasma polymerised stainless steel, with and without tropoelastin, was compared. DAPI stained cell nuclei (blue) were counted from 10 random fields and averaged for multiple samples (n=7). Attachment to the plasma polymerised surface alone, without protein showed no improvement, compared to control stainless steel (SS). However, immobilisation of tropoelastin on the polymerised surface produced an 86.3±10.5% (p<0.01 vs control) increase in HUVEC attachment.

C. Proliferation of Endothelial Cells on Coated Surfaces

Materials and Methods

The effect of protoelastin, fibronectin and bovine serum albumin (BSA), on human umbilical vein endothelial cell (HUVEC) growth was assessed in comparison to plastic alone. A 6 well plate was divided such that there were 3 time points (1, 2 and 3 days) for each treatment. Protoelastin, BSA and fibronectin were added such that each well received 2 ml/200 µg of protein. Plates were stored at 4° C. overnight, to allow adequate coating of the plate surfaces.

The next day, all protein solutions were removed from the wells. Approximately 40,000 HUVEC's were added to each well. The DMEM media was supplemented with 20% heat-inactivated human serum, glutamine, penicillin-streptomycin and pyruvate. Plates were incubated at 37° C., with 5% $CO_2$. At each time interval, solution was removed. Wells requiring further incubation were washed and supplied with fresh media. Wells ready for assay were washed three times with PBS and the number of cells was determined calorimetrically using One Solution Cell Proliferation Assay (Promega). Each well received 100 µl of fresh media and 20 µl of reagent, before incubation at 37° C., with 5% $CO_2$ for 90 min. Absorbance was read at 490 nm in a plate reader.

Results

Results showed fibronectin and protoelastin providing the best surface for the proliferation of HUVECs at 3 days (FIG. 10B). The proliferation of HUVECs over 7 days was assessed on tissue culture plastic (TCP), both control and plasma polymerised stainless steel. Surface immobilisation of tropoelastin improved endothelial cell proliferation by 36.3±12.2% at day 5 (p<0.05 vs untreated control) and 76.9±6.4% at day 7 (p<0.001). The cells had formed a confluent monolayer on the tropoelastin immobilised polymerised steel by day 7, while patches containing no cells were frequently observed on the control SS.

D. Endothelial Cell Proliferation on Plasma Polymerised Stainless Steel

Materials and Methods

HUVECs were prepared as described above and resuspended at 20,000 cells/mL. Cells were incubated for 3, 5 and 7 days at 37° C. in an atmosphere of 5% $CO_2$. At each time point, cells were fixed by adding 3.7% formaldehyde for 30 min at room temperature. The formaldehyde was aspirated and the wells washed three times with 500 µl PBS. Attached cells were stained by adding 100 µl 0.1% (w/v) crystal violet solution to each well for 1 h at room temperature. The crystal violet was aspirated and the wells washed once with 500 µl distilled (d) $H_2O$, followed by three times with 400 µl d$H_2O$. The dye was solubilised by the addition of 200 µl of 10% (v/v) acetic acid per well and 100 µl transferred to a 96-well plate and absorbance measured at 570 nm. Proliferation on tropoelastin immobilised plasma polymerised surfaces was compared to untreated stainless steel controls with no bound protein and uncoated tissue culture plastic.

Results

The proliferation of HUVECs over 7 days was assessed on tissue culture plastic (TCP), both control and plasma polymerised stainless steel (FIG. 10B). Surface immobilisation of tropoelastin improved endothelial cell proliferation by 36.3±12.2% at day 5 (p<0.05 vs untreated control) and 76.9±6.4% at day 7 (p<0.001). The cells had formed a confluent monolayer on the tropoelastin immobilised polymerised steel by day 7, while patches containing no cells were frequently observed on the control stainless steel.

E. Effect on Clotting

Materials and Methods

Clotting times for untreated SS and candidate-coated plasma polymerised steel (PPS) surfaces as determined by the Chandler loop assay. Surfaces were fitted into Tygon S-50-HL tubing and rotated for 85 min with heparinised blood at 34 rpm. Thrombi formation was initially assessed after 30, and 75 min rotation. After 75 min rotation, thrombi formation was assessed every 5 min.

Results

Figure 12:
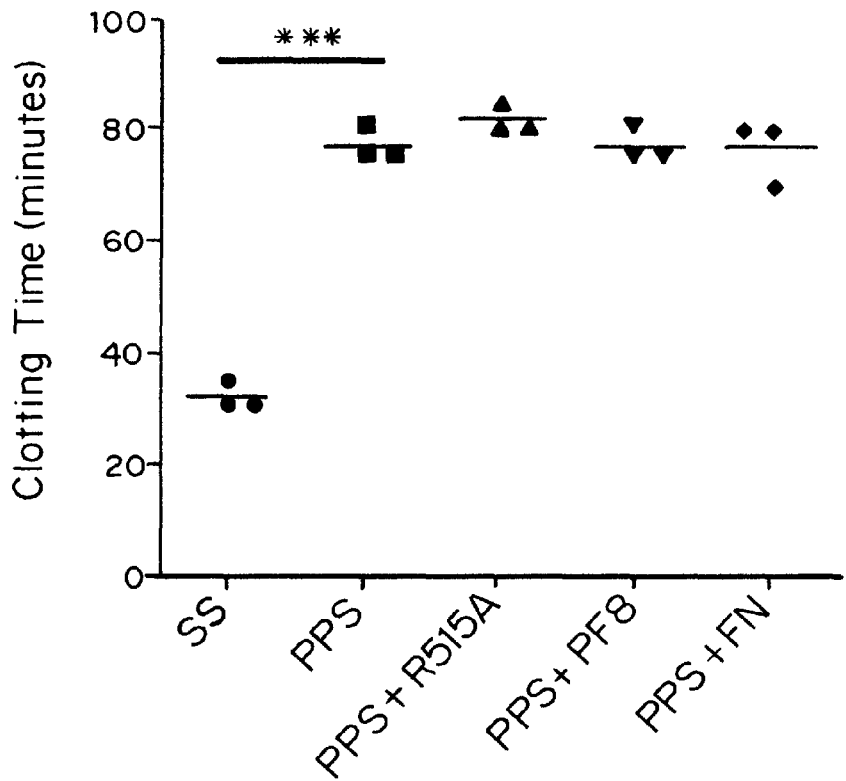
FIG. 12 is a graph of stainless steel (SS) surfaces' thrombogenicity under flow conditions as shown by time taken to clot formation. Clotting times for untreated SS and tropoelastin variant, PF8, or fibronectin-coated plasma polymerised steel (PPS) surfaces were determined using the Chandler loop assay. Surfaces were fitted into Tygon S-50-HL tubing and rotated for 85 min with heparinised blood at 34 rpm. Thrombi formation was initially assessed after 30, 35 and 75 min rotation. After 75 min rotation, thrombi formation was assessed every 5 min. R515A is a point mutant of tropoelastin with the potential for increased protease resistance; PF8 is recombinant fragment of fibrillin-1 and FN is fibronectin. This data shows that the non-thrombogenic properties of the PPS surface predominate, despite coating with three diverse proteins.

FIG. 12 is a graph of stainless steel (SS) surfaces' thrombogenicity under flow conditions as shown by time taken to clot formation. R515A is a point mutant of tropoelastin with the potential for increased protease resistance; PF8 is recombinant fragment of fibrillin-1 and FN is fibronectin. This data shows that the non-thrombogenic properties of the PPS surface predominate, despite coating with three diverse proteins.

Figure 13:
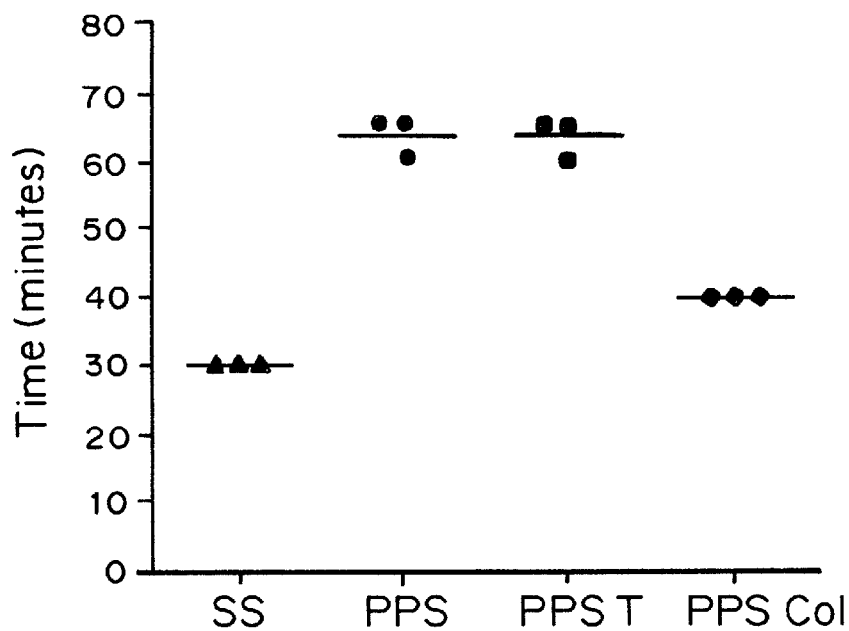
FIG. 13 is a graph of clotting under flow conditions. Clotting times for untreated SS and tropoelastin or collagen-coated plasma polymerised steel (PPS) surfaces as determined by the Chandler loop assay. Surfaces were fitted into Tygon S-50-HL tubing and rotated for 85 min with heparinised blood at 34 rpm.

FIG. 13 is a graph of clotting under flow conditions. While tropoelastin does not change the clotting time of coated PPS, collagen reduces it significantly. This shows that benefits of PPS alone and of PPS coated with tropoelastin.

Example 8

In Vivo Biocompatibility

Materials and Methods

Cellular responses to cross-linked tropoelastin were assessed 13 weeks after implantation in the dorsum of male guinea pigs, with collagen implants used as a control.

Results

Both cross-linked tropoelastin and collagen elicited a similar reaction that was limited to a typical cell mediated response to the presence of a foreign body. The observed cellular infiltrates did not suggest the presence of a specific immunological reaction. The collagen control had a short-lived duration following implantation and was largely dispersed by week four. The cross-linked tropoelastin samples were uniformly surrounded by fibrous encapsulation with minimal to moderate inflammation.

Example 9

Bioactivity Retention of Surface Attached IMP

Materials and Methods

Horseradish peroxidase (HRP) was immobilised on stainless steel foils and foils coated with three different polymerisation conditions (nitrogen, argon or both). The addition of argon to the acetylene alters the energetic ion bombardment occurring during the polymerisation, while nitrogen is incorporated into the film, modifying the chemical content and the intrinsic stress.

Results

Figure 11:
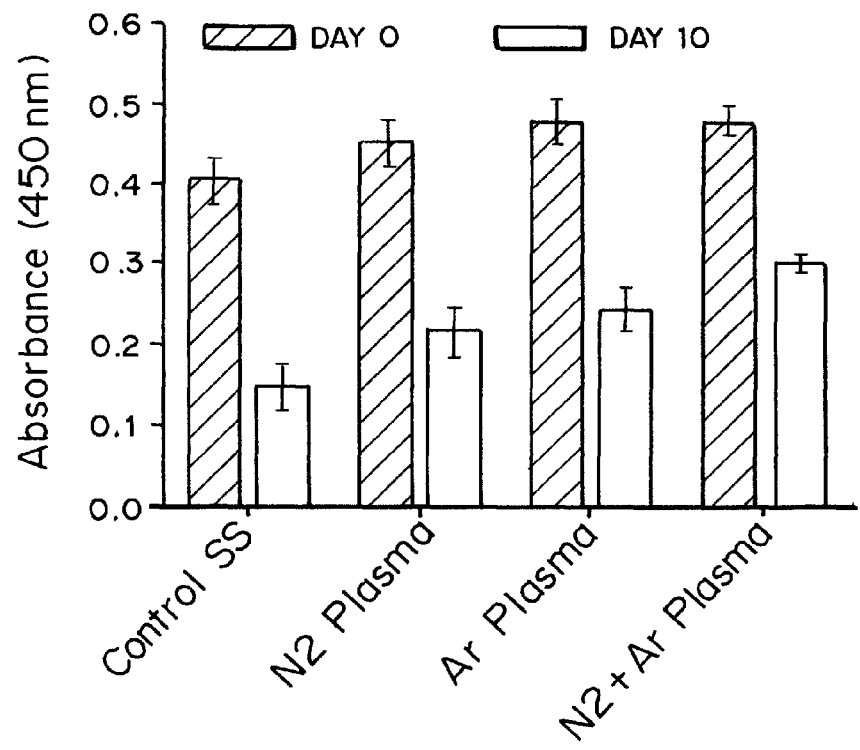
FIG. 11 is a graph showing the bioactivity of horseradish peroxidase (HRP) expressed as absorbance on three different treated surfaces over time. A mix of nitrogen and argon gas was found to create the surface with the greatest retention of HRP activity at 10 days.

The enzyme activity of HRP was found to be different across four sets of surfaces (FIG. 11). The first is the untreated control surface, while the remaining three sets have differences in the gas mixed with the acetylene precursor. All of the plasma coated samples had higher initial activity and much better retention of activity over 10 days compared to the uncoated steel control. Among the three groups of plasma deposited surfaces, the surface deposited with acetylene with nitrogen and argon flow appeared slightly better for maintaining activity to day 10.

Example 10

Resistance to Proteolytic Degradation of Tropoelastin Bound to PPS

Materials and Methods

Tropoelastin (1 mg/ml) was radiolabelled with $^{125}$I using Iodination Beads as per the manufacturer's instructions (Pierce). 1.2×0.8 cm pieces of SS or PPS were incubated with $^{125}$I tropoelastin overnight at 4° C. Protein coated samples were incubated with either PBS, heparinized plasma from a healthy volunteer (50% (v/v) with saline), 10 μM thrombin, or 22.5 μM kallikrein for 16 hours at 37° C. Samples were then washed and the radioactivity was counted using a scintillation counter. The metal samples were then washed with 5% SDS for 10 minutes at 90° C., washed and counted again.

Results

Figure 14:
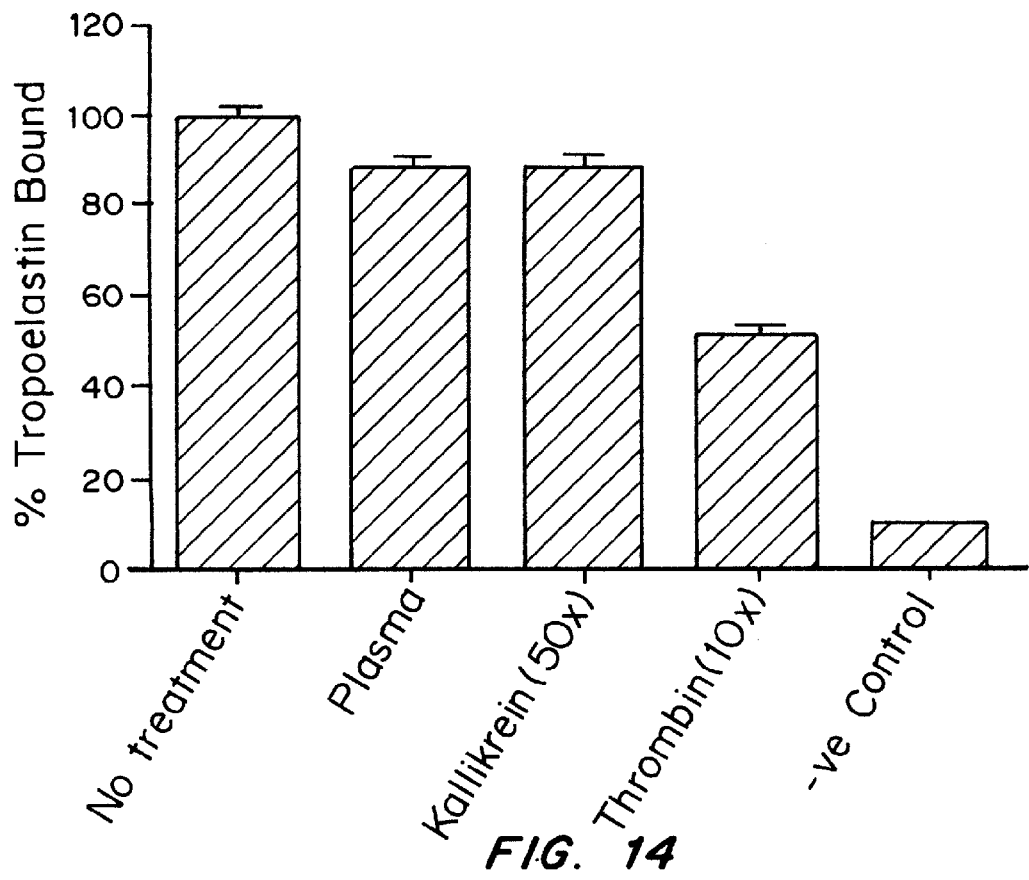
FIG. 14 is a graph of the percent tropoelastin remaining bound to coated PPS following treatment with plasma, kallikrein (50× plasma levels), thrombin (10× plasma levels)

This example demonstrates the resistance to degradation of tropoelastin coated PPS in the presence of various proteases. Treatment with blood plasma containing circulating proteases has minimal effect, as does a 50-fold excess of Kallikrein. Thrombin at 10× physiological concentration removes about half of the tropoelastin coating. See FIG. 14. This demonstrates that the protein remains bound to the PPS surface in vitro and has positive implications for the survival of the coating after implantation.

The covalently bound tropoelastin coating was found to be largely resistant to proteolytic degradation. Treatment with blood plasma containing normal circulating proteases has minimal effect, comparable to control levels of tropoelastin. The surface was also interrogated with common serum proteases kallekrein and thrombin. A 50-fold molar excess of Kallikrein compared to physiological levels was also comparable to control. Thrombin at 10× physiological concentration removes only about half of the tropoelastin coating. This in vitro assay demonstrates that the covalent immobilisation of tropoelastin on PPS renders it resistant to protease degradation and may increase its lifetime in vivo.

Modifications and variations of the present invention will be obvious to those skilled in the art from the foregoing detailed description and are intended to come within the scope of the appended claims. References cited herein are specifically incorporated by reference.

We claim:

1. A vascular medical device comprising a surface consisting of a plasma polymerized biocompatible polyhexane or polyacetylene having nitrogen incorporated therein on a metallic, ceramic, carbon or polymeric substrate of the device which contacts blood, wherein thrombogenicity of the substrate is decreased by the plasma polymerization in nitrogen or a mixture of argon and nitrogen.

2. The device of claim 1 having bound thereto a protein that is non-thrombogenic and promotes endothelial cell proliferation to the plasma polymerized surface.

3. The device of claim 2 wherein the protein is an extracellular matrix protein.

4. The device of claim 2 wherein the protein is a blend of tropoelastin and one or more polymers.

5. The device of claim 2 wherein the protein is crosslinked.

6. The device of claim 1 comprising one surface comprising polymeric material releasing a bioactive agent and another surface comprising a covalently bound protein.

7. The device of claim 6 wherein the protein surface is present under the surface releasing bioactive agent.

8. The device of claim 1 comprising a metal or carbon substrate.

9. The device of claim 1 which is degradable in whole or in part.

10. The device of claim 1 comprising a medical device selected from the group consisting of a stent, vascular conduit, a stent-graft, a surgically or percutaneously implantable heart valve, a vascular/septal occlusion device, and a vascular closure device.

11. The device of claim 1 further comprising at least one therapeutic, prophylactic, biomimetic or diagnostic agent.

12. The device of claim 1 comprising a laminate of protein on one or more layers of polymer.

13. The device of claim 12 wherein the laminate comprises alternating protein and polymer, wherein there may be more than one layer of polymer between layers of protein, and wherein there may be more than one type of polymer.

14. The device of claim 1 formed of or comprising a biodegradable metal or polymer.

15. The device of claim 1 comprising an elastin selected from the group consisting of elastin, protoelastin and tropoelastin.

16. The device of claim 15 wherein the elastin is selected from the group consisting of one or more crosslinked splice variants of tropoelastin, chemically modified tropoelastin, recombinant tropoelastin fragments, tropoelastin, a blend of tropoelastin with at least one additional polymeric material, and combinations thereof.

17. The device of claim 15 wherein the tropoelastin comprises one or more tropoelastins selected from the group consisting of full length tropoelastin;
  one or more splice variants of tropoelastin selected from the group consisting of an isoform lacking domains 22 and 26A and an isoform lacking domain 22, but including 26A;
  chemically modified tropoelastin selected from the group consisting of acetylated tropoelastin, pegylated tropoelastin, tropoelastin having a chemical or peptide linker attached thereto, and methylated tropoelastin; and
  recombinant tropoelastin fragments selected from the group consisting of a fragment encompassing the N-terminus domain but not all of the C-terminus domain, a fragment not encompassing all of the N-terminus domain or C-terminus domain, a fragment encompassing the C-terminus domain but not all of the N-terminus domain, R515A elastin, M155n and a fragment encompassing domain 36;
  wherein the tropoelastin is made by
  (a) covalently binding tropoelastin to a metal, ceramic, bone or polymeric substrate;
  (b) laminating tropoelastin to a synthetic non-natural polymer to form a tropoelastin-polymer laminate;
  (c) blending tropoelastin with a synthetic non-natural polymer; or
  (d) a combination thereof.

18. A body implantable medical device comprising a surface consisting of a nitrogen or mixture of argon and nitrogen plasma polymerized biocompatible polyhexane or polyacetylene surface having nitrogen incorporated therein on a metallic, ceramic, carbon or polymeric substrate of the device, comprising an extracellular matrix protein covalently bound to the plasma polymerized surface.

19. The device of claim 18 comprising an elastin selected from the group consisting of elastin, protoelastin and tropoelastin.

20. The device of claim 19 wherein the elastin is selected from the group consisting of one or more crosslinked splice variants of tropoelastin, chemically modified tropoelastin, recombinant tropoelastin fragments, tropoelastin, a blend of tropoelastin with at least one additional polymeric material, and combinations thereof.

21. The device of claim 20 wherein the tropoelastin comprises one or more tropoelastins selected from the group consisting of full length tropoelastin;
one or more splice variants of tropoelastin selected from the group consisting of an isoform lacking domains 22 and 26A and an isoform lacking domain 22, but including 26A;
chemically modified tropoelastin selected from the group consisting of acetylated tropoelastin, pegylated tropoelastin, tropoelastin having a chemical or peptide linker attached thereto, and methylated tropoelastin; and
recombinant tropoelastin fragments selected from the group consisting of a fragment encompassing the N-terminus domain but not all of the C-terminus domain, a fragment not encompassing all of the N-terminus domain or C-terminus domain, a fragment encompassing the C-terminus domain but not all of the N-terminus domain, R515A elastin, M155n and a fragment encompassing domain 36;
wherein the tropoelastin is made by
(a) covalently binding tropoelastin to a metal, ceramic, bone or polymeric substrate;
(b) laminating tropoelastin to a synthetic non-natural polymer to form a tropoelastin-polymer laminate;
(c) blending tropoelastin with a synthetic non-natural polymer; or
(d) a combination thereof.

22. The device of claim 18 wherein the medical device is a matrix for tissue engineering, bone implant or prosthetic, implantable pump, microchip or electrode.

23. A method for manufacturing a vascular medical device, comprising plasma polymerizing polyhexane or polyacetylene in nitrogen or a mixture of argon and nitrogen to form polyhexane or polyacetylene having nitrogen incorporated therein on a polymeric, metallic, ceramic or carbon surface or component of the device which contacts blood, wherein the thrombogenicity of the substrate is decreased by the plasma polymerized surface.

24. The method of claim 23 wherein the substrate is a metal or carbon.

25. The method of claim 24 wherein the metal is selected from the group consisting of stainless steel, nitinol, tantalum, nickel, cobalt, chromium, rhenium, molybdenum, platinum, titanium, and alloys thereof.

26. The method of claim 23 comprising covalently attaching a protein to a surface of the device wherein the protein is co-incubated with the plasma polymerized surface and covalently attached to the surface.

* * * * *